(12) United States Patent
Weigl et al.

(10) Patent No.: US 8,168,782 B2
(45) Date of Patent: May 1, 2012

(54) PROCESSES FOR THE PREPARATION OF 8-CHLORO-1-METHYL-2,3,4,5-TETRAHYDRO-1H-3-BENZAZEPINE AND INTERMEDIATES RELATED THERETO

(75) Inventors: Ulrich Weigl, Hilzingen (DE); Frank Porstmann, Stetten (CH); Christoph Straessler, Reigoldswil (CH); Lars Ulmer, Neunkirch (CH); Ulf Koetz, Tengen (DE)

(73) Assignee: Arena Pharmaceuticals, Inc., San Diego, CA (US)

( * ) Notice: Subject to any disclaimer, the term of this patent is extended or adjusted under 35 U.S.C. 154(b) by 748 days.

(21) Appl. No.: 12/225,966

(22) PCT Filed: Apr. 2, 2007

(86) PCT No.: PCT/US2007/008170
§ 371 (c)(1),
(2), (4) Date: Jan. 14, 2009

(87) PCT Pub. No.: WO2007/120517
PCT Pub. Date: Oct. 25, 2007

(65) Prior Publication Data
US 2009/0143576 A1   Jun. 4, 2009

Related U.S. Application Data

(60) Provisional application No. 60/789,191, filed on Apr. 3, 2006.

(51) Int. Cl.
*C07D 223/16* (2006.01)
(52) U.S. Cl. ...................................................... 540/594
(58) Field of Classification Search .................... 540/594
See application file for complete search history.

(56) References Cited

U.S. PATENT DOCUMENTS

| | | |
|---|---|---|
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,856,503 A | 1/1999 | Aebi et al. |
| 5,861,393 A | 1/1999 | Danilewicz et al. |
| 5,925,651 A | 7/1999 | Hutchinson |
| 5,939,415 A | 8/1999 | Laufer et al. |
| 5,942,535 A | 8/1999 | Laufer et al. |
| 5,958,543 A | 9/1999 | Teng et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,514,422 B2 | 4/2009 | Smith et al. |
| 7,704,993 B2 | 4/2010 | Smith et al. |
| 7,977,329 B2 | 7/2011 | Smith et al. |
| 2007/0060568 A1 | 3/2007 | Smith et al. |
| 2007/0275949 A1 | 11/2007 | Smith et al. |
| 2008/0045502 A1* | 2/2008 | Wolgast et al. ........... 514/217.01 |
| 2009/0143576 A1 | 6/2009 | Weigl et al. |
| 2010/0004223 A1* | 1/2010 | Agarwal et al. .......... 514/217.01 |
| 2010/0173894 A1 | 7/2010 | Brian et al. |
| 2010/0305316 A1 | 12/2010 | Gharbaoui et al. |

FOREIGN PATENT DOCUMENTS

| | | |
|---|---|---|
| AU | 515236 | 1/1988 |
| CA | 1090797 | 12/1980 |
| CA | 2197789 A1 | 2/1996 |
| CH | 500194 | 1/1971 |
| DE | 1 944 121 | 3/1970 |
| DE | 19 14 456 | 6/1971 |
| DE | 33 15 106 A1 | 11/1983 |
| DE | 34 18 270 A1 | 11/1985 |
| EP | 0 007 070 B1 | 1/1983 |
| EP | 0 161 350 A1 | 11/1985 |
| EP | 0 174 118 A2 | 3/1986 |
| EP | 0 080 779 B1 | 7/1986 |

(Continued)

OTHER PUBLICATIONS

U.S. Appl. No. 60/479,280, filed Jun. 17, 2003, Aytes et al.
U.S. Appl. No. 60/512,967, filed Oct. 21, 2003, Aytes et al.
U.S. Appl. No. 60/789,191, filed Apr. 3, 2006, Freifeld et al.
U.S. Appl. No. 61/268,930, filed Jun. 18, 2009, Carlos et al.
Baindur et al., "(+)-3-allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).
Barnes, Pharmacological Strategies for Relapse Prevention in Schizophrenia, Psychiatry, 3(10):37-40 (2004).
Bickerdike, "5-HT2C Receptor Agonists as Potential Drugs for the Treatment of Obesity," Current Topics in Medicinal Chemistry, vol. 3:885-897 (2003).

(Continued)

*Primary Examiner* — Brenda Coleman
(74) *Attorney, Agent, or Firm* — Foley & Lardner LLP

(57) ABSTRACT

The present invention provides processes, methods and intermediates for the preparation of 8-chloro-1-methyl-2,3,4,5-tetrahydro-1H-3-benzazepine, salts, hydrates and crystal forms thereof which are useful as serotonin (5-HT) receptor agonists for the treatment of, for example, central nervous system disorders such as obesity.

27 Claims, No Drawings

FOREIGN PATENT DOCUMENTS

| | | |
|---|---|---|
| EP | 0 204 349 A2 | 12/1986 |
| EP | 0 096 838 B1 | 4/1987 |
| EP | 0 285 287 A3 | 10/1988 |
| EP | 0 285 919 A1 | 10/1988 |
| EP | 0 987 235 B1 | 3/2003 |
| EP | 1 074 549 B1 | 11/2003 |
| GB | 1 196 229 | 6/1970 |
| GB | 1 221 324 | 2/1971 |
| GB | 1 225 053 | 3/1971 |
| GB | 1 247 306 | 9/1971 |
| GB | 1 268 243 | 3/1972 |
| GB | 1 599 705 | 10/1981 |
| GB | 2 133 401 A | 7/1984 |
| JP | 62-267250 | 11/1987 |
| JP | 02-502723 | 8/1990 |
| JP | 05-339263 | 12/1993 |
| JP | 06-298746 | 10/1994 |
| JP | 08-134048 | 5/1996 |
| JP | 09-030960 | 2/1997 |
| JP | 2000-044533 | 2/2000 |
| JP | 2001-089472 | 4/2001 |
| NL | 7807819 | 1/1980 |
| SU | 1238732 A3 | 6/1986 |
| WO | WO 88/07858 A1 | 10/1988 |
| WO | WO 91/19698 A1 | 12/1991 |
| WO | WO 93/00094 A2 | 1/1993 |
| WO | WO 95/13274 A1 | 5/1995 |
| WO | WO 96/04271 A1 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/062392 A2 | 7/2003 |
| WO | WO 03/086306 A2 | 10/2003 |
| WO | WO 2004/037788 A1 | 5/2004 |
| WO | WO 2005/003096 A1 | 1/2005 |
| WO | WO 2005/019179 A2 | 3/2005 |
| WO | WO 2005/042490 A1 | 5/2005 |
| WO | WO 2005/042491 A1 | 5/2005 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2007/120517 A2 | 10/2007 |
| WO | WO 2008/070111 A2 | 6/2008 |
| WO | WO 2009/111004 A1 | 9/2009 |

OTHER PUBLICATIONS

Bosch et al., "Studies on the Synthesis of Pentacyclic Strychnos Indole Alkaloids. Photocyclization of N-Chloroacetyl-1,2,3,4,5,6-hexahydro-1,5-methanoazocino [4,3-b] Indole Derivatives," Tetrahedron, 41(12):2557-66 (1985).
Bremner, "Seven Membered Rings," Institute for Biomolecular Science Dept. of Chemistry, University of Wollongong; "Progress in Heterocyclic Chemistry 13", Pergamon Press, Ch. 7:340-77 (2001).
Casy et al., "Some Arylalkylamino Analogs of Acyclic Analgetics", J Med Chem, (1968), 11(3):599-601.
Chahal et al., IDdb Meeting Report 2000, May 17-18.
Chang et al., "Dopamine Receptor Binding Properties of Some 2,3,4,5-Tetrahydro-1H-3-Benzazepine-7-ols With Non-Aromatic Substituents In The 5-Position", Bioorganic & Med. Chem. Letters, (1992) 2(5);399-402.
Chumpradit et al., "( )-7-chloro-8-hydroxyl-1-(4'-[125I]iodophenyl)-3-methyl-2,3,4,5-tetrahydro-1H-3-benzazepine: A Potential CNS D-1 Dopamine Receptor Imaging Agent," J. Med. Chem., 32:1431-5 (1989).
Clark et al., "1,9-alkano-bridged 2,3,4,5-tetrahydro-1H-3-benzzazepines with Affinity for the FJDK-Adrenoceptor and the 5-HT1A Receptor," J. Med. Chem., 33:633-41 (1990).

Deady, et al., "Synthesis of some tetrahydro-2-and 3-benzazepines, and of hexahydro-3-benzazocine," Journal of the Chemical Society, Perkins Transactions 1, 1973, pp. 782-783.
Demarinis et al., "Development of an Affinity Ligand for Purification of KDAKLJ-Adrenoceptors from Human Platelet Membranes," J. Med. Chem., 27, 918-21 (1984).
Di Chiara et al., "Reward System and Addiction: What Dopamine Does and Doesn't Do", Current Opinion in Pharmacology 7:69-76 (2007).
Di Chiara, "Nucleus accumbens shell and core dopamine: differential role in behavior and addiction." (2002) Behavioural Brain Research, 137: 75-114.
Di Giovanni et al., "Serotonin/dopamine interaction—Focus on 5-HT2c receptor, a new target of psychotropic drugs," Indian Journal of Experimental Biology, vol. 40:1344-1352 (2002).
Di Matteo et al., "Role of 5-HT.sub.2C Receptors in the Control of Central Dopamine Function", Trends in Pharmacological Sciences 22(5):229-232 (2001).
Diagnostic and Statistical Manual of Mental Disorders, 4th edition, Text Revision,Washington, DC, American Psychiatric Association, 2000.
Dixit et al., "Gents Acting on Central Nervous System: Part XXIII- 2-Substitutes 1,2,3,4,6,7,12,12a-Ochtahydropyrazino[2,I-b][3] benzazepines & 3-substituted 1,2,3,4,4a,5,6,11-Octahydropyrazin[I,2-b][2] benzazepines," CDRI Communication No. 1969, 893-97, (1974).
Draper et al., "Novel Stereoselective Syntheses of the Fused Benzazepine Dopamine D1 Antagonist (6aS, 13bR)-11-chloro-6, 6a,7,8,9, 13b-hexahydro-7-methyl-5H-benzo[d]naphth[2,1-b]axepin-12-ol (Sch 39166):1. Aziridinium Salt Based Syntheses," Organic Process Research & Development, 2(3):175-85 (1998).
Flannery-Schroeder, "Reducing Anxiety to Prevent Depression," Am. J. Prev. Med. 31(6S1):S136-S142 (2006).
Fuchs et al., "Total Synthesis of (+/−)-Lennoxamine And (+/−)-Aphanorphine By Intramolecular Electrophilic Aromatic Substitution Reactions Of 2-Amidoacroleins," Organic Letters, 2001, pp. 3923-3925, 3(24).
Gallant et al., "U-22,394A: a controlled evaluation in chronic schizophrenic patients," Current Therapy Research, 9(11):579-81(1967).
Gardent et al., "Sur quelques de l'amino-2-bromo-4 1H benzazepine-3 et de ses derives," Bull Soc. Chim. France (1968) 2:600-605.
Gerace et al., "Predictors of Weight Increases over 7 Years in Fire Fighters and Paramedics," Preventive Medicine, 25:593-600 (1996).
Gerritz et al., "Two General Routes to 1,4-disubstituted-2,3,4,5-tetrahydro-1H-3-benzazepines," Organic Letters, 2(25):4099-102 (2000).
Gobert et al., "Serotonin2c Receptors Tonically Suppress the Activity of Mesocortical Dopaminergic and Adrenergic, But Not Serotonergic, Pathways: A Combined Dialysis And Electrophysiological Analysis in the Rat," Synapse, 36:205-221 (2000).
Gombar et al., "Pharmacokinetics of a series of 6-chloro-2, 3, 4, 5-tetrahydro-3-substituted--1H-3-benzazepines in rats," Drug Metab. Disposition (1988) 16:367-372.
Greene et al., Protective Groups in Organic Synthesis, 2.sup.nd Ed., Wiley and Sons, NY 1991.
Griesser, "Polymorphism in the Pharmaceutical Industry," ed. Rolf Hilfiker, Wiley,VCH Verlag GmbH & Co.: pp. 211-233 (2006).
Guillory, "Polymorphism in Pharmaceutical Solids," ed. Harry G. Brittain, Marcel Dekker, Inc., vol. 95: pp. 202-209 (1999).
Halford et al., "Serotonergic Drugs: Effects on Appetite Expression and Use for the Treatment of Obesity," Drugs, 67(1):27-55 (2007).
Halford, "Obesity Drugs in Clinical Development," Current Opinion in Investigational Drugs 7(4):312-318 (2006).
Hasan et al., "Syntheses of N-chloroacyl-beta-phenylethylamine Derivatives," Indian J. Chem., 9:1022-4 (1971).
Hassine-Coniac et al., "Preparation et properietes d'aldehydes dans la serie de la benzazapine-3," Bull Soc. Chim. Fance (1971) 11:3985-3992.
Hazebroucq "Acces a des I-H, tetrahydro-2, 3, 4, 5 benzazepines-3 one-1 et a des hexahydro imidazo isoquinoleines," Ann. Chim. (1966) pp. 221-254.

Helferich et al., "Uber Derivate Einger Chinolincarbonsauren," J. Fur Praktische Chemie, vol. 33, 1966, 39-48.

Hester et al., "Azepinoindoles. I. Hexahyclroazepino[4,5-b]indoles," J. Med. Chem, 11(1):101-106 (1968).

Heys et al., "A New Entry into C7-Oxygenated Tetrahydro-1H-3-benzazepines:Efficient Labeling with Carbon-14 in the Benzo Ring," J. Org. Chem., 54(19):4702-6 (1989).

Higgins et al,, "Serotonin and drug reward: focus on 5-HT2c receptors," European Journal of Pharmacology, 480:151-162, (2003).

Hitzig, "Combined Serotonin and Dopamine Indirect Agonistscorrectalcohol Craving and Alcohol-Associated Neuroses," Journal of Substance Abuse Treatment, 11(5):489-90 (1994).

Im et al., "Positive Allosteric Modulator of the Human 5-HT2C Receptor," MolecularPharmacology, 64: 78-84 (2003).

International search report for international application No. PCT/US2003/011076 dated Oct. 16, 2003.

International Search Report for International Application No. PCT/US2005/046983 dated Jan. 26, 2007.

Jenck et al., "Antiaversive effects of 5-HT2c receptor agonists and fluoxetine in a model of panic-like anxiety in rats," European Neuropsychopharmacology, 8:161(1998).

Jensen et al., "Potential Role of New Therapies in Modifying Cardiovascular Risk in Overweight Patients with Metabolic Risk Facts", Obesity 14 (Suppl. 3):143S-149S (2006).

Kaiser et al., "6-(Phenylthio)-substituted 2,3,4,5-tetrahydro-1H-3-benzazepines, a Novel Class of Dopamine Receptor Antagnoists and Neuroleptics," J. Med. Chem., 23(9):975-6 (1980).

Karasu et al., (2000) Practice Guideline for the Treatment of Patients with MajorDepressive Disorder.

Klohr et al., "An Intramolecular Photocyclization to Form the Azepino[3,4,5-cd]Indole System," Synthetic Communications 18(7):671-4 (1988).

Koplan et al., "Preventing Childhood Obesity: Health in the Balance, Executive Summary", http://www.nap.edu/catalog/11015.html, 41 pages (2005).

Kuenburg et al., "Development of a Pilot Scale Process for the Anti-Alzheimer Drug (-)-Galantahmine Using Large-Scale Phenolic Oxidative Coupling and Crystallisation-Induced Chiral Conversion," Organic Process Research & Development, 3(6):425-31 (1999).

Lacivita et al., "Selective Agents for Serotonin2C (5-HTC2C) Receptor," Current Topics in Medicinal Chemistry, vol. 6:pp. 1927-1970 (2006).

Ladd et al., "Synthesis and Dopaminergic Binding of 2-Aryldopamine Analogues: Phenethylamines, 3-Benzazepines, and 9-(Aminomethyl)flourenes", J. Med. Chem., (1986) 29(10):1904-1912.

Lam et al., (1999) (eds) Canadian Consensus Guidelines for the Treatment ofSeasonal Affective Disorder, Clinical & Academic Publishing, Vancouver, BC, Canada.

Lennon et al., "Azabenzocycloheptenones. Part XVIII. Amines and amino-ketones of the tetrahydro-3-benzazepine-1-one series," J. Chem. Soc. Perkin Transacts. (1975) 7:622-626.

Lin et al., "Benzindene Prostaglandins. Synthesis of Optically Pure 15-Deoxy-U-68,215 and its Enantiomer via a Modified Intramolecular Wadsworth-Emmons-Witting Reaction," J. Org. Chem., 52(25):5594-601 (1987).

MacDonald et al., "Design and synthesis of trans-3-(2-(4-((3-(3-(5-methyl-1,2,4-oxadiazolyl))-phenyl)carboxamido)cyc- I ohexyl)ethyl)-7-methylsulfonyl-2,3,4,5-tetrahydro-1H-3-benzazepine (SB-414796): A Potent and selective dopamine D3 Receptor Antagonist," J. Med. Chem., 2003, 4952-4964, vol. 46, American Chemical Society.

Moline et al., "Postpartum Depression: A Guide for Patients and Families," ExpertConsensus Guidelines Series—Treatment of Depression in Woman 2001, Mar. 112-113 (2001).

Muller et al., "Intracellular 5-HT2C-receptor Dephosphorylation: A New Target for Treating Drug Addiction," Trends in Pharmacological Sciences, 27(9):455-58 (2006).

Nagase et al., "An anhydrous polymorphic form of trehalose," Carbohydrate Research 337(2),167-173 (2002) (Abstract).

Nagle et al., "Efficient Synthesis of beta-amino Bromides," Tetrahedron Letters, 41:3011-4 (2000).

Nair et al., "Prepartion of 2,3,4,5-tetrahydro-3,1H-benzazepine-2-one," Indian J. Chem., 5:169-70 (1967).

National Institute on Drug Abuse, Proceedings of the 41st Annual Scientific Meeting (1979) pp. 356-401.

Navarro-Vazquez et al., "A study of aryl radical cyclization in enaminone esters", J. Org. Chem. 67:3213-20 (2002).

Neumeyer et al., "Development of a High Affinity and Stereoselective Photoaffinity Label for the D-1 Dopamine Receptor: Synthesis and Resolution of 7-[125I]Iodo-8-hydroxy-3-methyl-1-(4'-azidophenyl)-2,3,4,5-tetrahydro-1H-3-benzazepine," J. Med. Chem., 33(2):521-6 (1990).

Niendam et al., "Neurocognitive Performance and Functional Disability in the Psychosis Prodrome," Schizophrenia Research, 84:100-111 (2006).

Office Action for U.S. Appl. No. 10/560,953, dated Aug. 17, 2010.

Office Action for U.S. Appl. No. 11/599,050 dated Aug. 20, 2010.

Office Action for U.S. Appl. No. 11/793,941 dated Sep. 17, 2010.

Okuno et al., "Photocyclization of N-chloroacetyl-2,5-dimethoxyphenethylamine Synthesis of Pyrroloindoles," Chem. Pharm. Bull., 23(11):2584-90 (1975).

Orito et al., Hokkaido Daigaku Kogakubu Kenkyu Hokoku (1979), (96), 41-44.

Orito et al., "Alkylation of 1,2,4,5-Terahydro-3-methyl-3H-3-Benzazepin-2-One with Sodium Hydride and Alkyl Halide," Tetrahedron 36:1017-1021 (1980) Pergamon Press Ltd.

Orito et al., "Total Synthesis of Pseudo Type of Protopine Alkaloids," Heterocycles 14(1), 11-14 (1980).

Orito et al., "Synthetic studies of heterocyclic compounds I. Alkylation and acylation of 1,2,4,5-tetrahydro-3-methyl-3H-3-benzazepin-2-one," CASREACT, 1979, 93:7990.

Pauvert et al., "Silver Nitrate-Promoted Ring Enlargement of 1-Tribromomethyl-1,2-dihydro- and 1-Tribromomethyl-1,2,3,4-tetrahydro-isoquinoline Derivatives: Application to the Synthesis of the Anti-anginal Zatebradine," Tetrahedron Letters, 44:4203-6 (2003), Pergamon Press Ltd.

Pawan et al., "Preliminary study on the effects of fenfluramine derivative, 'S992' inman," British Journal of Pharmacology, 41(2): 416P-417P (1971) (CAPLUS abstract).

Pecherer et al., "A Novel Synthesis of Aromatic Methoxy and Methylenedioxy Substituted 2,3,4,5-tetrahydro-1H-3-benzaepines," J. Het. Chem., 9:609-16 (1972).

Pecherer et al., "The Synthesis of Some 7- and 7,8-substituted 2,3,4,5-tetrahydro-1H-3-benzazepines," J. Heterocyclic Chemistry 8(5):779-783 (1971).

Perry et al., "Prospective study of risk factors for development on non-insulin dependent diabetes in middle aged British men," BMJ (1995) 310:560-564.

Pfeiffer et al., "Dopaminergic Activity of Substituted 6-chloro-1-phenyl-2,3,4,5-tetrahydro-1H-3-benzazepines," J. Med. Chem., 25(4):352-8 (1982).

Piesla et al, (2001), Schizophrenia Research, 49:95.

Porras et al., "5-HT2a and 5-HT2c/2b Receptor Subtypes Modulate Dopamine ReleaseInduced in Vivo by Amphetamine and Morphine in Both the Rat Nucleus Accumbensand Striatum," Neuropsychopharmacology, 26: 311-324 (2002).

Prous Science Integrity entry 156186, 2007.

Prous Science Integrity entry 354056, 2007.

Remington's Pharmaceutical Sciences, 17th ed., Mack Publishing Company, Easton Pa.: 1418 (1985).

Rothman, "Treatment of alcohol and cocaine addiction by the combination of pemoline and fenfluramine: a preliminary case series." (1995) Journal of Substance Abuse Treatment, 12(6): 449-453.

Schaffner et al., "Preventing Severe Mental Illnesses—New Prospects and Ethical Challenges," Schizophrenia Research, 51:3-15 (2001).

Schlademan et al., "Synthesis of oxo- and 1-hydroxy-azobenzocycloalkanes," J. Chem. Soc. Perkin Transacts. (1972) 2:213-215.

Smith et al., "Discovery and SAR of New Benzepines as Potent and Selective 5HT2c Receptor Agonists for the Treatment of Obesity," Bioorganic & Medicinal Chemistry Letters, 15(5):1467-1470 (2005).

Smith et al., "Discovery and Structure—Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," [retrieved on Dec. 21, 2007]. Retrieved from the Internet. <URL:http://pubs.acs.orgijournals/jmcmar/index.html>.

Tietze et al., "Efficient Synthesis of 2,3,4,5-tetrahydro-1H-3-benzazepines by intermolecular heck Reaction," Institut fur Organische Chemie der Universtat Gottingen, Tammannstrasse 2, D-3400 Gottingen, Germany, received Jan. 29, 1993.

Tsuang et al., Towards the Prevention of Schizophrenia, B245 Biol. Psychiatry, 48:349-356 (2000).

Van Oekelen et al., "5-HT2A and 5-HT2C receptors and their atypical regulation properties," Life Sciences, vol. 72:2429-2449 (2003).

Vanderlaan et al., "Synthesis and Oxidative Coupling of ( )-3-oxoreticuline," J. Org. Chem., 50(6):743-7 (1985).

Vink et al., "Risk Factors for Anxiety and Depression in the Elderly: A Review", J. Affect. Disord., doi:10.1016/j.jad.2007.06.005, 16 pages (2007).

Weinstock et al., "Separation of Potent Central and Renal Dopamine Agonist Activity in Substituted 6-chloro-2,3,4,5-tetrahydro-7,8-dihydroxy-1-phenyl-1H-3-benzazepines," J. Med. Chem., 23(9):973-5 (1980).

Williams, Chemistry Demystified 123 (2003).

Wise, "Addiction becomes a brain disease", (2000) Neuron, 26: 27-33.

Wisner et al., "Clinical practice. Postpartum depression." (2002) N. Engl. J. Med., 347(3): 194-199.

Wu et al., "Amino Diol Based Asymmetric Syntheses of a Fused Benzazepine as a Selective D1 Dopamine Receptor," Organic Process Research & Development, 1(5):359-64 (1997).

Yasuda et al., "A Novel and Stereoselective Synthesis of ( )-cephalotaxine and its Analogue," Tetrahedron Letters, 27(18):2023-6 (1986).

Yonemitsu et al., "Photocyclization of Pharmacodynamic Amines. IV. Novel Heterocycles from N-chloroacetyl-3,4-dimethoxyphenethylamine," Journal of the American Chemical Society, 92(19):5686-90 (1970).

Yonemitsu et al., "Photocyclization of Pharmodynamic Amines. II. X-Ray Analysis of a Noncentrosymmetric Tetracyclic Indole," Journal of the American Chemical Society, 90(23):6522-3 (1968).

Yonemitsu et al., "Photocyclizations of Tyrosines, Tyramines, Catecholamines, and Normescaline," Journal of the American Chemical Society, 90(3):776-84 (1968).

Yonemitsu et al., "Photolysis of N-Chloracetyle-O-methyl-L-tyrosine to an Azaazulene," Journal of the American Chemical Society, 89(4):1039-40 (1967).

Yoshinaga et al., "Prevention of Mildly Overweight Children from Development of More Overweight Condition," Prevention Medicine, 38:172-174 (2004).

* cited by examiner

PROCESSES FOR THE PREPARATION OF 8-CHLORO-1-METHYL-2,3,4,5-TETRAHYDRO-1H-3-BENZAZEPINE AND INTERMEDIATES RELATED THERETO

CROSS REFERENCE TO RELATED APPLICATIONS

This application is a 35 USC §371 National Stage application based on International App. No. PCT/US2007/008170, filed Apr. 2, 2007, which claims the priority benefit of U.S. Ser. No. 60/789,191, filed Apr. 3, 2006.

FIELD OF THE INVENTION

The present invention provides processes, methods and intermediates for the preparation of 8-chloro-1-methyl-2,3,4,5-tetrahydro-1H-3-benzazepine, salts, hydrates and crystal forms thereof which are useful as serotonin (5-HT) receptor agonists for the treatment of, for example, central nervous system disorders such as obesity.

BACKGROUND OF THE INVENTION

Serotonin (5-HT) neurotransmission plays an important role in numerous physiological processes both in health and in psychiatric disorders. For example, 5-HT has been implicated in the regulation of feeding behavior. 5-HT is believed to work by inducing a feeling of fullness or satiety so eating stops earlier and fewer calories are consumed. It has been shown that a stimulatory action of 5-HT on the $5HT_{2C}$ receptor plays an important role in the control of eating and in the anti-obesity effect of d-fenfluramine. As the $5\text{-}HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective $5\text{-}HT_{2C}$ receptor agonist can be a more effective and safe anti-obesity agent. Also, $5\text{-}HT_{2C}$ knockout mice are overweight with cognitive impairment and susceptibility to seizure. Thus, the $5HT_{2C}$ receptor is recognized as a well-accepted receptor target for the treatment of obesity, psychiatric, and other disorders.

In view of the growing demand for compounds for the treatment of disorders related to the $5\text{-}HT_{2C}$ receptor, new and more efficient routes to 3-benzazepines are needed. The processes and compounds described herein help meet these and other needs.

SUMMARY OF THE INVENTION

The processes and intermediates of the present invention are useful in the preparation of therapeutic agents for the treatment or prophylaxis of 5-HT mediated disorders such as obesity and other central nervous system diseases.

The present invention provides, inter alia, processes and intermediates for preparing 8-chloro-1-methyl-2,3,4,5-tetrahydro-1H-3-benzazepine having Formula (I), salts and crystal form thereof:

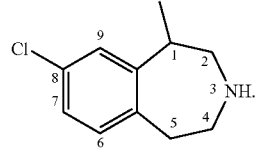

(I)

In some embodiments, the compound of Formula (I) is the R enantiomer.

DETAILED DESCRIPTION OF EMBODIMENTS OF THE INVENTION

The processes and intermediates of the present invention are useful in the preparation of the therapeutic agents of Formula (I), salts and crystal form thereof. Compounds of Formula (I) are useful for the treatment or prophylaxis of 5-HT associated disorders such as obesity and other central nervous system diseases.

In some embodiments, [2-(4-chloro-phenyl)-ethyl]-(2-chloro-propyl)-ammonium chloride is the starting material for the preparation of 8-chloro-1-methyl-2,3,4,5-tetrahydro-1H-3-benzazepine, HCl salts and a crystal form thereof.

Certain processes for the preparation of Compounds of Formula (I) and salts thereof are disclosed in PCT Patent Publication, WO2005/019179. One particular process has been disclosed for the preparation of a certain crystal form of the Compound of Formula (Ia) in PCT Patent Publication, WO2006/069363.

Several improvements have now been discovered for the processes useful in the preparation of Compounds of Formula (I), salts and crystal form thereof. These improvements are described herein.

Conversion of Commercially Available Compound, 2-(4'-chlorophenyl)ethanol to [2-(4 chloro-phenyl)-ethyl]-(2-chloro-propyl)-ammonium Chloride (Stages 1 to 3)

In some embodiments, [2-(4-chloro-phenyl)-ethyl]-(2-chloro-propyl)-ammonium chloride can be prepared in three stages from the commercially available compound, 2-(4'-chlorophenyl)ethanol, according to the process depicted in Synthetic Scheme 1.1.

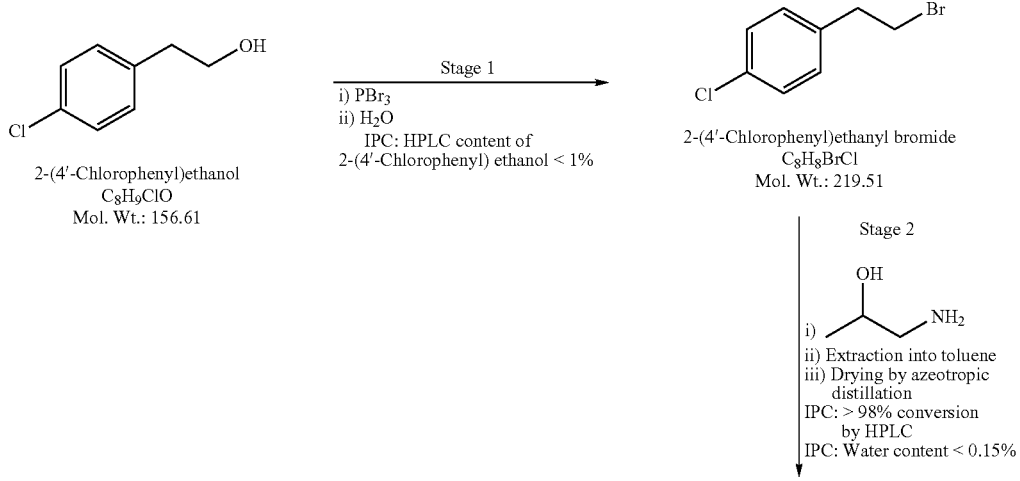

3

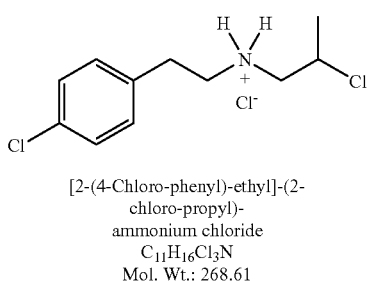

[2-(4-Chloro-phenyl)-ethyl]-(2-chloro-propyl)-ammonium chloride
$C_{11}H_{16}Cl_3N$
Mol. Wt.: 268.61

Stage 3
i) $SOCl_2$, Toluene, Catalytic DMA
ii) Filtration and toluene wash
iii) Recystallization from IPA/$H_2O$
IPC: HPLC purity for information only

4

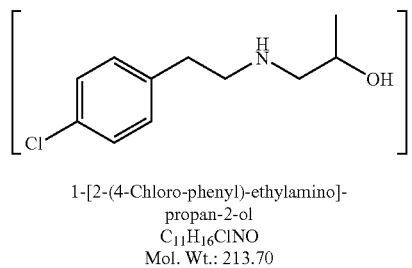

1-[2-(4-Chloro-phenyl)-ethylamino]-propan-2-ol
$C_{11}H_{16}ClNO$
Mol. Wt.: 213.70

In some embodiments, the product that is prepared from a stage is not isolated. In some embodiments, 1-[2-(4-chlorophenyl)-ethylamino]-propan-2-ol is converted to [2-(4-chloro-phenyl)-ethyl]-(2-chloro-propyl)-ammonium chloride without isolation.

Stage 1—Conversion of 2-(4'-chlorophenyl)ethanol to 2-(4'-chlorophenyl)ethyl Bromide In Stage 1, the 2-(4'-chlorophenyl)ethanol was reacted with phosphorous tribromide to give 2-(4'-chlorophenyl)ethyl bromide. The product was isolated directly from an aqueous quench without the need of an extractive solvent.

Some embodiments of the present invention provide methods for preparing 2-(4'-chlorophenyl)ethyl bromide comprising reacting 2-(4'-chlorophenyl)ethanol with phosphorous tribromide for a time and under conditions suitable for forming 2-(4'-chlorophenyl)ethyl bromide.

In some embodiments, 2-(4'-chlorophenyl)ethyl bromide is prepared by the method comprising reacting 2-(4'-chlorophenyl)ethanol with phosphorous tribromide in the absence of solvent.

In some embodiments, 2-(4'-chlorophenyl)ethyl bromide is prepared by the method of reacting 2-(4'-chlorophenyl)ethanol with phosphorous tribromide comprising the steps:
adding phosphorous tribromide to 2-(4'-chlorophenyl)ethanol at a temperature of less than about 10° C. to form a bromination reaction mixture; and
heating the bromination reaction mixture at a temperature of about 20° C. to about 30° C. and subsequently at a temperature of about 75° C. to about 85° C.

In some embodiments, 2-(4'-chlorophenyl)ethyl bromide is prepared by the method comprising heating the bromination reaction mixture at a temperature of about 20° C. to about 30° C. and is maintained at this temperature for about 1 hour to about 3 hours.

In some embodiments, 2-(4'-chlorophenyl)ethyl bromide is prepared by the method comprising heating the bromination reaction mixture at a temperature of about 75° C. to about 85° C. and is maintained at this temperature for about 2 hour to about 4 hours to form a mixture comprising 2-(4'-chlorophenyl)ethyl bromide.

In some embodiments, 2-(4'-chlorophenyl)ethyl bromide is prepared by the method comprising the steps:
adding water to the mixture comprising 2-(4'-chlorophenyl)ethyl bromide at a temperature of about 5° C. to about 20° C. to form a biphasic liquid mixture consisting essentially of an upper aqueous phase and a lower phase comprising 2-(4'-chlorophenyl)ethyl bromide; and
separating the lower phase comprising 2-(4'-chlorophenyl) ethyl bromide of the biphasic liquid mixture from the upper aqueous phase of the biphasic liquid mixture.

In some embodiments, 2-(4'-chlorophenyl)ethyl bromide is prepared by the method wherein the lower phase comprising the 2-(4'-chlorophenyl)ethyl bromide is substantially pure.

The phrase "2-(4'-chlorophenyl)ethyl bromide is substantially pure", as used herein, refers to the level of purity sufficient to be used in the next stage without further purification to prepare 1-[2-(4-chloro-phenyl)-ethylamino]-propan-2-ol.

In some embodiments, the lower phase comprising 2-(4'-chlorophenyl)ethyl bromide has a purity of about 90% or greater.

In some embodiments, the lower phase comprising 2-(4'-chlorophenyl)ethyl bromide has a purity of about 95% or greater.

In some embodiments, the lower phase comprising 2-(4'-chlorophenyl)ethyl bromide has a purity of about 98% or greater.

Some embodiments of the present invention provide methods for preparing 2-(4'-chlorophenyl)ethyl bromide comprising reacting 2-(4'-chlorophenyl)ethanol with phosphorous tribromide for a time and under conditions suitable for forming 2-(4'-chlorophenyl)ethyl bromide, wherein reacting is carried out at about 75° C. to about 85° C.

Some embodiments of the present invention provide methods for preparing 2-(4'-chlorophenyl)ethyl bromide comprising reacting 2-(4'-chlorophenyl)ethanol with phosphorous tribromide for a time and under conditions suitable for forming 2-(4'-chlorophenyl)ethyl bromide, wherein the time is for about 120 minutes to about 240 minutes.

Some embodiments of the present invention provide methods for preparing 2-(4'-chlorophenyl)ethyl bromide comprising reacting 2-(4'-chlorophenyl)ethanol with phosphorous tribromide for a time and under conditions suitable for forming 2-(4'-chlorophenyl)ethyl bromide, wherein 2-(4'-chlorophenyl)ethyl bromide is isolated by the addition of water.

Stage 2—Conversion of 2-(4'-chlorophenyl)ethyl Bromide to 1-[2-(4-chloro-phenyl)-ethylamino]-propan-2-ol In Stage 2, 2-(4'-chlorophenyl)ethyl bromide was reacted with 1-amino-2-propanol to form the secondary amine, 1-[2-(4-chloro-phenyl)-ethylamino]-propan-2-ol. 1-[2-(4-Chlorophenyl)-ethylamino]-propan-2-ol was separated from excess 1-amino-2-propanol and water soluble byproducts by extraction into toluene and removing water from the toluene containing 1-[2-(4-Chloro-phenyl)-ethylamino]-propan-2-ol by azetropic distillation and can be used directly into the next step without further purification and without isolation.

Some embodiments of the present invention are methods for preparing 1-[2-(4-chloro-phenyl)-ethylamino]-propan-2-ol comprising reacting 2-(4'-chlorophenyl)ethyl bromide and 1-amino-2-propanol for a time and under conditions suitable for forming 1-[2-(4-chloro-phenyl)-ethylamino]-propan-2-ol or a salt thereof.

In some embodiments, 1-[2-(4-chloro-phenyl)-ethylamino]-propan-2-ol is substantially a free base.

In some embodiments, 1-[2-(4-chloro-phenyl)-ethylamino]-propan-2-ol is prepared by the method comprising reacting 2-(4'-chlorophenyl)ethyl bromide and 1-amino-2-propanol for a time and under conditions suitable for forming an alkylation mixture comprising 1-[2-(4-chloro-phenyl)-ethylamino]-propan-2-ol.

In some embodiments, 1-[2-(4-chloro-phenyl)-ethylamino]-propan-2-ol is prepared by the method comprising the steps:

adding water to the alkylation mixture comprising 1-[2-(4-chloro-phenyl)-ethylamino]-propan-2-ol to form a biphasic mixture;

extracting 1-[2-(4-chloro-phenyl)-ethylamino]-propan-2-ol from the biphasic mixture with an extracting solvent comprising toluene to form a new biphasic mixture consisting essentially of an aqueous lower phase and an upper phase comprising toluene and 1-[2-(4-chloro-phenyl)-ethylamino]-propan-2-ol;

separating the upper phase comprising toluene and 1-[2-(4-chloro-phenyl)-ethylamino]-propan-2-ol from the aqueous lower phase; and removing water from the upper phase comprising toluene and 1-[2-(4-chloro-phenyl)-ethylamino]-propan-2-ol by azeotropic distillation to form a solution comprising toluene and 1-[2-(4-chloro-phenyl)-ethylamino]-propan-2-ol.

In some embodiments, 1-[2-(4-chloro-phenyl)-ethylamino]-propan-2-ol is prepared by the method wherein the solution comprising toluene and 1-[2-(4-chloro-phenyl)-ethylamino]-propan-2-ol after azeotropic distillation contains about 2% water or less.

In some embodiments, 1-[2-(4-chloro-phenyl)-ethylamino]-propan-2-ol is prepared by the method wherein the solution comprising toluene and 1-[2-(4-chloro-phenyl)-ethylamino]-propan-2-ol after azeotropic distillation contains about 1% water or less.

In some embodiments, 1-[2-(4-chloro-phenyl)-ethylamino]-propan-2-ol is prepared by the method wherein the solution comprising toluene and 1-[2-(4-chloro-phenyl)-ethylamino]-propan-2-ol after azeotropic distillation contains about 0.5% water or less.

In some embodiments, 1-[2-(4-chloro-phenyl)-ethylamino]-propan-2-ol is prepared by the method wherein the solution comprising toluene and 1-[2-(4-chloro-phenyl)-ethylamino]-propan-2-ol after azeotropic distillation contains about 0.15% water or less.

In some embodiments, 1-[2-(4-chloro-phenyl)-ethylamino]-propan-2-ol is prepared by the method comprising reacting 2-(4'-chlorophenyl)ethyl bromide and 1-amino-2-propanol for a time and under conditions suitable for forming an alkylation mixture comprising 1-[2-(4-chloro-phenyl)-ethylamino]-propan-2-ol, wherein reacting is carried out at about 85° C. to about 100° C.

In some embodiments, 1-[2-(4-chloro-phenyl)-ethylamino]-propan-2-ol is isolated by an aqueous extraction in the presence of toluene, whereby 1-amino-2-propanol and water soluble byproducts are removed and the resulting toluene solution of product is dried by azeotropic distillation.

Stage 3—Conversion of 1-[2-(4-chloro-phenyl)-ethylamino]-propan-2-ol to [2-(4-chloro-phenyl)-ethyl]-(2-chloro-propyl)-ammonium chloride In Stage 3, the final step to prepare [2-(4-chloro-phenyl)-ethyl]-(2-chloro-propyl)-ammonium chloride, 1-[2-(4-chloro-phenyl)-ethylamino]-propan-2-ol was reacted with thionyl chloride in toluene with N,N-dimethylacetamide (DMA) as a catalyst.

The crude product was isolated from the reaction mixture by filtration and recrystallized from isopropanol (IPA) and water. The filtered solid [2-(4-chloro-phenyl)-ethyl]-(2-chloro-propyl)-ammonium chloride was washed with IPA and dried under vacuum. It has now been discovered that isopropanol (IPA) can be used to quench any excess thionyl chloride and the solid resulting after the quench surprisingly does not require a recrystallization step.

Some embodiments of the present invention provide methods for preparing [2-(4-chloro-phenyl)-ethyl]-(2-chloro-propyl)-ammonium chloride comprising reacting 1-[2-(4-chloro-phenyl)-ethylamino]-propan-2-ol and thionyl chloride for a time and under conditions suitable for forming [2-(4-chloro-phenyl)-ethyl]-(2-chloro-propyl)-ammonium chloride.

In some embodiments, [2-(4-chloro-phenyl)-ethyl]-(2-chloro-propyl)-ammonium chloride is prepared comprising the steps:

determining that 1-[2-(4-chloro-phenyl)-ethylamino]-propan-2-ol is substantially converted to [2-(4-chloro-phenyl)-ethyl]-(2-chloro-propyl)-ammonium chloride; and in a subsequent step quenching any residual amount of thionyl chloride with a $C_{1-6}$ alcohol.

In some embodiments, the $C_{1-6}$ alcohol is isopropanol.

In some embodiments, in the determining step it is determined that the 1-[2-(4-chloro-phenyl)-ethylamino]-propan-2-ol is converted to [2-(4-chloro-phenyl)-ethyl]-(2-chloro-propyl)-ammonium chloride in an amount of about 98% or greater.

In some embodiments, the amount of 1-[2-(4-chloro-phenyl)-ethylamino]-propan-2-ol that is converted to [2-(4-chloro-phenyl)-ethyl]-(2-chloro-propyl)-ammonium chloride is determined by HPLC.

In some embodiments, [2-(4-chloro-phenyl)-ethyl]-(2-chloro-propyl)-ammonium chloride is prepared in the presence of N,N-dimethylacetamide as a catalyst.

In some embodiments, the mole ratio of N,N-dimethylacetamide to 1-[2-(4-chloro-phenyl)-ethylamino]-propan-2-ol is about 0.5 to 1 or less.

In some embodiments, the mole ratio of N,N-dimethylacetamide to 1-[2-(4-chloro-phenyl)-ethylamino]-propan-2-ol is about 0.4 to 1 or less.

In some embodiments, the mole ratio of N,N-dimethylacetamide to 1-[2-(4-chloro-phenyl)-ethylamino]-propan-2-ol is about 0.3 to 1 or less.

In some embodiments, the mole ratio of N,N-dimethylacetamide to 1-[2-(4-chloro-phenyl)-ethylamino]-propan-2-ol is about 0.2 to 1 or less.

In some embodiments, the mole ratio of N,N-dimethylacetamide to 1-[2-(4-chloro-phenyl)-ethylamino]-propan-2-ol is about 0.1 to 1 or less.

In some embodiments, [2-(4-chloro-phenyl)-ethyl]-(2-chloro-propyl)-ammonium chloride is prepared in the presence of a solvent comprising toluene.

In some embodiments, after the quenching step the [2-(4-chloro-phenyl)-ethyl]-(2-chloro-propyl)-ammonium chloride is isolated by filtration.

In some embodiments, [2-(4-chloro-phenyl)-ethyl]-(2-chloro-propyl)-ammonium chloride is prepared by the method comprising reacting 1-[2-(4-chloro-phenyl)-ethylamino]propan-2-ol and thionyl chloride for a time and under conditions suitable for forming [2-(4-chloro-phenyl)-ethyl]-

(2-chloro-propyl)-ammonium chloride; wherein reacting is carried out at a temperature of about 60° C. to about 65° C.

In some embodiments, [2-(4-chloro-phenyl)-ethyl]-(2-chloro-propyl)-ammonium chloride is prepared by the method comprising reacting 1-[2-(4-chloro-phenyl)-ethylamino]-propan-2-ol and thionyl chloride for a time and under conditions suitable for forming [2-(4-chloro-phenyl)-ethyl]-(2-chloro-propyl)-ammonium chloride, wherein [2-(4-chloro-phenyl)-ethyl]-(2-chloro-propyl)-ammonium chloride crystallizes from the reaction mixture and is isolated by filtration.

In some embodiments, [2-(4-chloro-phenyl)-ethyl]-(2-chloro-propyl)-ammonium chloride is isolated with a purity of about 85% or greater.

In some embodiments, [2-(4-chloro-phenyl)-ethyl]-(2-chloro-propyl)-ammonium chloride is isolated with a purity of about 90% or greater.

In some embodiments, [2-(4-chloro-phenyl)-ethyl]-(2-chloro-propyl)-ammonium chloride is isolated with a purity of about 95% or greater.

In some embodiments, [2-(4-chloro-phenyl)-ethyl]-(2-chloro-propyl)-ammonium chloride is isolated with a purity of about 98% or greater.

In some embodiments, [2-(4-chloro-phenyl)-ethyl]-(2-chloro-propyl)-ammonium chloride is isolated with a purity of about 99% or greater.

Stage 4—Conversion of [2-(4-chloro-phenyl)ethyl]-(2-chloro-propyl)-ammonium chloride to 8-chloro-1-methyl-2,3,4,5-tetrahydro-1H-benzazepine In Stage 4, the starting material, [2-(4-chloro-phenyl)-ethyl]-(2-chloro-propyl)-ammonium chloride, typically about 90.0%, and in some embodiments greater than 99.0% purity, undergoes an intramolecular Friedel-Crafts-cyclization to provide the racemic mixture designated as 8-chloro-1-methyl-2,3,4,5-tetrahydro-1H-benzazepine, consisting of a 1:1 mixture of (R)- and (S)-8-chloro-1-methyl-2,3,4,5-tetrahydro-1H-benzazepine (free base). The backbone of the 8-chloro-1-methyl-2,3,4,5-tetrahydro-1H-benzazepine was established during this reaction. 8-Chloro-1-methyl-2,3,4,5-tetrahydro-1H-benzazepine was purified by solvent extractions and removal of solvent by distillation. 8-Chloro-1-methyl-2,3,4,5-tetrahydro-1H-benzazepine was obtained as an oil with a typical purity of 3540% for the desired enantiomer, (R)-8-chloro-1-methyl-2,3,4,5-tetrahydro-1H-benzazepine (free base).

The improvements for Stage 4 centers around the isolation of the 8-chloro-1-methyl-2,3,4,5-tetrahydro-1H-benzazepine. Here, instead of using NaOH as reported in WO2005/019179, water and silica get is used which is simply filtered. Furthermore, the mixture after filtration surprisingly forms a triphasic mixture (three layers), wherein the bottom layer consists mostly of 1,2-dichlorobenzene and only about 1% of 8-chloro-1-methyl-2,3,4,5-tetrahydro-1H-benzazepine. Therefore, the bulk of 1,2-dichlorobenzene can easily be removed from the mixture by simply draining the bottom layer away from the middle and top layers. Surprisingly, the middle layer consists mostly of the product, (R,S)-8-chloro-1-methyl-2,3,4,5-tetrahydro-1H-benzazepine, and is easily isolated by draining the middle layer from the aqueous top layer. The isolated middle layer is about 90% 8-chloro-1-methyl-2,3,4,5-tetrahydro-1H-benzazepine. The top layer contains about 1% to about 4% of 8-chloro-1-methyl-2,3,4,5-tetrahydro-1H-benzazepine and can be isolated by extracting with an appropriate solvent, for example, cyclohexane. The formation of the triphasic mixture improves the volume efficiency for this stage and also eliminates the need for evaporating of the reaction solvent (i.e., 1,2-dichlorobenzene).

Some embodiments of the present invention provide methods for preparing 8-chloro-1-methyl-2,3,4,5-tetrahydro-1H-benzazepine comprising reacting [2-(4-chloro-phenyl)-ethyl]-(2-chloro-propyl)-ammonium chloride with AlCl$_3$ for a time and under conditions suitable for forming 8-chloro-1-methyl-2,3,4,5-tetrahydro-1H-benzazepine.

Some embodiments of the present invention provide methods for preparing a compound of Formula (I):

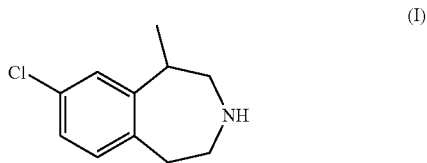

(I)

wherein reacting [2-(4-chloro-phenyl)-ethyl]-(2-chloro-propyl)-ammonium chloride with AlCl$_3$ is carried out in the presence of 1,2-dichlorobenzene at a temperature of about 125° C. to about 130° C. for about 14 hours to about 18 hours under conditions suitable for forming the compound of Formula (I).

Some embodiments of the present invention provide methods for preparing a compound of Formula (I):

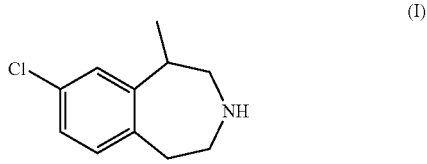

(I)

comprising the steps:
reacting [2-(4-chloro-phenyl)-ethyl]-(2-chloro-propyl)-ammonium chloride with AlCl$_3$ in the presence of 1,2-dichlorobenzene at a temperature of about 120° C. to about 135° C. for about 14 hours to about 18 hours under conditions suitable for forming a crude reaction mixture comprising the compound of Formula (I);

contacting the crude reaction mixture with silica gel and water to form a suspension;

filtering the suspension to form a triphasic liquid mixture; and isolating the compound of Formula (I) from the triphasic liquid mixture.

Some embodiments of the present invention provide methods for preparing a compound of Formula (I) further comprising the steps:

separating the top phase and the middle phase from the bottom phase of the triphasic liquid mixture; and isolating the compound of Formula (I) from the top phase and the middle phase.

Some embodiments of the present invention provide methods for preparing a compound of Formula (I) wherein the bottom phase of the triphasic liquid mixture comprises 1,2-dichlorobenzene.

In some embodiments, the bottom phase of the triphasic liquid mixture contains 1,2-dichlorobenzene in an amount of about 90% or greater.

In some embodiments, the bottom phase of the triphasic liquid mixture contains 1,2-dichlorobenzene in an amount of about 95% or greater.

In some embodiments, the bottom phase of the triphasic liquid mixture contains 1,2-dichlorobenzene in an amount of about 98% or greater.

Some embodiments of the present invention provide methods for preparing a compound of Formula (I) wherein the middle phase of the triphasic liquid mixture contains the compound of Formula (I) in an amount greater than the amount of the compound of Formula (I) contained in the top phase or the bottom phase of the triphasic liquid mixture.

Some embodiments of the present invention provide methods for preparing a compound of Formula (I) wherein the middle phase of the triphasic liquid mixture contains the compound of Formula (I) in an amount of about 80% or greater.

In some embodiments, the middle phase of the triphasic liquid mixture contains the compound of Formula (I) in an amount of about 85% or greater.

In some embodiments, the middle phase of the triphasic liquid mixture contains the compound of Formula (I) in an amount of about 90% or greater.

Some embodiments of the present invention provide methods for preparing a compound of Formula (I) wherein the isolating step further comprises the steps:

separating the top phase from the middle phase;

extracting the compound of Formula (I) from the top phase with an extracting solvent and separating the extracting solvent comprising the compound of Formula (I) from the top phase;

combining the extracting solvent comprising the compound of Formula (I) together with the middle phase to form a combined mixture;

washing the combined mixture with a basic, aqueous solution and separating the basic, aqueous solution from the combined mixture to form a washed, combined solution; and concentrating the washed, combined solution to provide the compound of Formula (I).

Some embodiments of the present invention provide methods for preparing a compound of Formula (I) wherein the basic solution is aqueous sodium hydroxide.

In some embodiments, the basic, aqueous solution is about 10% to about 40% aqueous sodium hydroxide.

In some embodiments, the basic, aqueous solution is about 25% to about 35% aqueous sodium hydroxide.

In some embodiments, the basic, aqueous solution is about 30% aqueous sodium hydroxide.

In some embodiments, the compound of Formula (I) is about 65% pure or greater after the concentration step.

In some embodiments, the compound of Formula (I) is about 70% pure or greater after the concentration step.

Some embodiments of the present invention provide methods for preparing a compound of Formula (I) wherein the extracting solvent is cyclohexane.

Some embodiments of the present invention provide methods for preparing 8-chloro-1-methyl-2,3,4,5-tetrahydro-1H-benzazepine comprising reacting [2-(4-chloro-phenyl)-ethyl]-(2-chloro-propyl)-ammonium chloride with $AlCl_3$ for a time and under conditions suitable for forming 8-chloro-1-methyl-2,3,4,5-tetrahydro-1H-benzazepine, wherein reacting is carried out at about 125° C. to about 130° C.

Some embodiments of the present invention provide methods for preparing 8-chloro-1-methyl-2,3,4,5-tetrahydro-1H-benzazepine comprising reacting [2-(4-chloro-phenyl)-ethyl]-(2-chloro-propyl)-ammonium chloride with $AlCl_3$ for a time and under conditions suitable for forming 8-chloro-1-methyl-2,3,4,5-tetrahydro-1H-benzazepine, wherein reacting is carried out at about 128° C.

Some embodiments of the present invention provide methods for preparing 8-chloro-1-methyl-2,3,4,5-tetrahydro-1H-benzazepine comprising reacting [2-(4-chloro-phenyl)-ethyl]-(2-chloro-propyl)-ammonium chloride with $AlCl_3$ for a time and under conditions suitable for forming 8-chloro-1-methyl-2,3,4,5-tetrahydro-1H-benzazepine, wherein reacting is carried out for a time of about 14 hours to about 18 hours.

In-process control (IPC): HPLC content of [2-(4-chloro-phenyl)-ethyl]-(2-chloro-propyl)-ammonium chloride <1%. This stage is depicted in Synthetic Scheme 1.2.

Synthetic Scheme 1.2

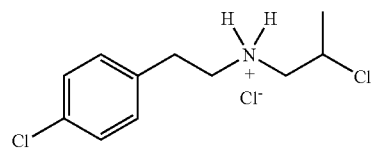

[2-(4-Chloro-phenyl)-ethyl]-(2-chloro-propyl)-ammonium chloride
$C_{11}H_{16}Cl_3N$
Mol. Wt.: 268.61 i) $AlCl_3$, 1,2-Dichlorobenzene, 128° C.
ii) $H_2O$, $SiO_2$
iii) Aq. NaOH, Cyclohexane Stage 4

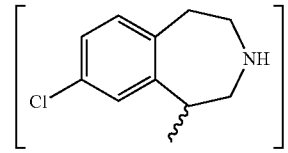

8-Chloro-1-methyl-2,3,4,5-tetrahydro-1H-benzo[d]azepine (1:1 Racemic mixture)
$C_{11}H_{14}ClN$
Mol. Wt.: 195.69

Stage 5 and Stage 6—Conversion of 8-Chloro-1-methyl-2,3,4,5-tetrahydro-1H-benzazepine to (R)-8-Chloro-1-methyl-2,3,4,5-tetrahydro-1H-benzo[d]azepinium Hemitartrate In Stage 5, 8-chloro-1-methyl-2,3,4,5-tetrahydro-1H-benzazepine was reacted with L-(+)-tartaric acid to form the crude diastereomeric salt (R)-8-chloro-1-methyl-2,3,4,5-tetrahydro-1H-benzo[d]azepinium hemitartrate. In this stage, the resolution and purification of (R)-8-chloro-1-methyl-2,3,4,5-tetrahydro-1H-benzo[d]azepinium hemitartrate from process impurities, including the opposite enantiomer (i.e., S-enantiomer), was obtained by crystallization from an acetone/water mixture. The isolated cake typically had an achiral purity of greater than 99.0% and a chiral purity of 90% enantiomeric excess (ee).

In Stage 6, the (R)-8-chloro-1-methyl-2,3,4,5-tetrahydro-1H-benzo[d]azepinium hemitartrate crude cake was subjected to a second crystallization from acetone/water to afford the final intermediate, (R)-8-chloro-1-methyl-2,3,4,5-tetrahydro-1H-benzo[d]azepinium hemitartrate. (R)-8-Chloro-1-methyl-2,3,4,5-tetrahydro-1H-benzo[d]azepinium hemitartrate was tested and released to specifications and typically had an achiral purity of 100.0% and a chiral purity of greater than 99.0% ee. Additional recrystallization of (R)-8-chloro-1-methyl-2,3,4,5-tetrahydro-1H-benzo[d]azepinium Hemitartrate from acetone/water can be repeated at this stage, if required, to increase % ee.

In the procedure reported in WO2005/019179, the solvent used in the salt forming step was t-butanol. The use of this solvent resulted in the crystallization of the crude hemitartrate with approximately 68-80% ee and less than about 99% ee after the singly recrystallized hemitartrate. An additional recrystallization was required to increase the % ee and as a result a decreased in the yield.

It has now been discovered that using acetone in the salt forming step, instead of t-butanol as described in WO2005/019179, eliminates the need for an additional recrystallization and also has a direct result on improving the yield. Accordingly, using acetone resulted in about 90% ee (compared to about 68-80% ee using t-butanol) and after only one recrystallization the hemitrate was about 99% or greater and in general about 99.7% ee.

Some embodiments of the present invention provide methods for resolving a mixture of compounds of (R)/(S)-8-chloro-1-methyl-2,3,4,5-tetrahydro-1H-benzazepine comprising contacting the mixture of compounds with L-(+)-tartaric acid to form chiral resolving acid salts of the compounds, wherein the chiral resolving acid comprises substantially one stereoisomer; and precipitating the chiral resolving acid salts of the compounds, wherein the resulting precipitate is enriched in the chiral resolving acid salt of (R)-8-chloro-1-methyl-2,3,4,5-tetrahydro-1H-benzazepine.

Some embodiments of the present invention provide methods for resolving a mixture of compounds of Formul (Ia) and (Ib):

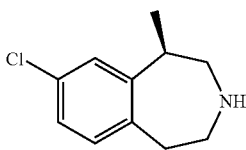

(Ia)

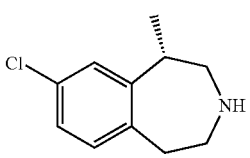

(Ib)

comprising:
contacting the mixture of compounds with L-(+)-tartaric acid in the presence of a solvent comprising acetone to form L-(+)-tartaric acid salts of the compounds;
precipitating the L-(+)-tartaric acid salts of the compounds, wherein the resulting precipitate is enriched with the L-(+)-tartaric acid salt of the compound of Formula (Ia);
dissolving the precipitate in a solution comprising acetone and water to form a solution containing the dissolved precipitate;
cooling the solution containing the dissolved precipitate; and
precipitating a second precipitate containing the L-(+)-tartaric acid salt of the compound of Formula (Ia).

Some embodiments of the present invention provide methods for resolving a mixture of compounds of Formula (Ia) and (Ib):

comprising:
contacting the mixture of compounds with L-(+)-tartaric acid in the presence of a solvent comprising acetone to form L-(+)-tartaric acid salts of the compounds;
precipitating the L-(+)-tartaric acid salts of the compounds, wherein the resulting precipitate is enriched with the L-(+)-tartaric acid salt of the compound of Formula (Ia);
dissolving the precipitate in a solution comprising acetone and water at a temperature of about 45° C. to about 60° C. to form a solution containing the dissolved precipitate;
cooling the solution containing the dissolved precipitate to a temperature of about −5° C. to about 10° C.; and
precipitating a second precipitate containing the L-(+)-tartaric acid salt of the compound of Formula (Ia) with an enantiomeric excess of about 98% or greater.

In some embodiments, dissolving the precipitate in a solution comprising acetone and water is carried out at a temperature of about 45° C. to about 60° C. to form a solution containing the dissolved precipitate.

In some embodiments, cooling the solution containing the dissolved precipitate is carried out a temperature of about −5° C. to about 110° C.

In some embodiments, methods of the present invention include dissolving the precipitate in a solution comprising acetone and water at a temperature of about 55° C. to about 60° C. to form a solution containing the precipitate.

In some embodiments, methods of the present invention include cooling the solution containing the precipitate to a temperature of about 0° C. to about 5° C.

In some embodiments, the second precipitate containing the L-(+)-tartaric acid salt of the compound of Formula (Ia) has an enantiomeric excess of about 98% or greater.

In some embodiments, the second precipitate containing the L-(+)-tartaric acid salt of the compound of Formula (Ia) has an enantiomeric excess of about 98.5% or greater.

In some embodiments, the second precipitate containing the L-(+)-tartaric acid salt of the compound of Formula (Ia) has an enantiomeric excess of about 99% or greater.

In some embodiments, contacting the mixture of compounds with L-(+)-tartaric acid in the presence of a solvent comprising acetone is carried out at about 40° C. to about 55° C.

In some embodiments, contacting the mixture of compounds with L-(+)-tartaric acid in the presence of a solvent comprising acetone is carried out at about 47° C. to about 52° C.

IPC: Quantification of 8-chloro-1-methyl-2,3,4,5-tetrahydro-1H-benzazepine content; IPC: Chiral HPLC of wet product. This stage is depicted in Synthetic Scheme 1.3.

Synthetic Scheme 1.3

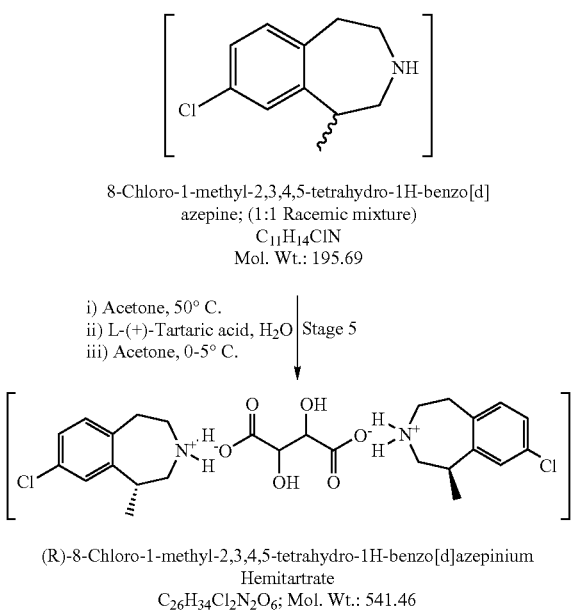

8-Chloro-1-methyl-2,3,4,5-tetrahydro-1H-benzo[d]
azepine; (1:1 Racemic mixture)
$C_{11}H_{14}ClN$
Mol. Wt.: 195.69 i) Acetone, 50° C.
ii) L-(+)-Tartaric acid, $H_2O$  | Stage 5
iii) Acetone, 0-5° C.

(R)-8-Chloro-1-methyl-2,3,4,5-tetrahydro-1H-benzo[d]azepinium
Hemitartrate
$C_{26}H_{34}Cl_2N_2O_6$; Mol. Wt.: 541.46
IPC: Chiral HPLC of wet product > 98% ee. This stage is depicted inSynthetic Scheme

Synthetic Scheme 1.4

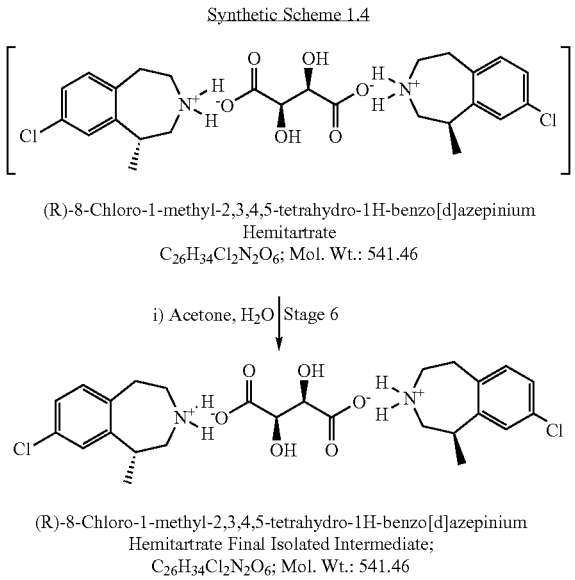

(R)-8-Chloro-1-methyl-2,3,4,5-tetrahydro-1H-benzo[d]azepinium
Hemitartrate
$C_{26}H_{34}Cl_2N_2O_6$; Mol. Wt.: 541.46 i) Acetone, $H_2O$ | Stage 6

(R)-8-Chloro-1-methyl-2,3,4,5-tetrahydro-1H-benzo[d]azepinium
Hemitartrate Final Isolated Intermediate;
$C_{26}H_{34}Cl_2N_2O_6$; Mol. Wt.: 541.46

Stage 7—Conversion of (R)-8-chloro-1-methyl-2,3,4,5-tetrahydro-1H-benzo[d]azepinium Hemitartrate to (R)-8-chloro-1-methyl-2,3,4,5-tetrahydro-1H-3-benzazepine Hydrochloride Hemihydrate In Stage 7, the enantiomerically pure (R)-8-chloro-1-methyl-2,3,4,5-tetrahydro-1H-benzo[d]azepinium hemitartrate, from Stage 6, was converted to the (R)-8-chloro-1-methyl-2,3,4,5-tetrahydro-1H-3-benzazepine hydrochloride hemihydrate in two additional chemical reactions that involved formation of (R)-8-chloro-1-methyl-2,3,4,5-tetrahydro-1H-3-benzazepine free base and finally (R)-8-chloro-1-methyl-2,3,4,5-tetrahydro-1H-3-benzazepine hydrochloride hemihydrate. (R)-8-chloro-1-methyl-2,3,4,5-tetrahydro-1H-3-benzazepine hydrochloride hemihydrate then underwent a final purification by crystallization from ethyl acetate. (R)-8-chloro-1-methyl-2,3,4,5-tetrahydro-1H-3-benzazepine hydrochloride hemihydrate was isolated as a crystalline solid and typically has an achiral purity of about 100.0% and a chiral purity of about 99.0% ee or greater. In some embodiments, achiral purity is about 98% or greater and a chiral purity of about 98% ee or greater.

The processes for the preparation of (R)-8-chloro-1-methyl-2,3,4,5-tetrahydro-1H-3-benzazepine hydrochloride hemihydrate and anhydrous (R)-8-chloro-1-methyl-2,3,4,5-tetrahydro-1H-3-benzazepine hydrochloride were reported in PCT patent publications WO2006/069363 and WO2005/019179 respectively. The (R)-8-chloro-1-methyl-2,3,4,5-tetrahydro-1H-3-benzazepine hydrochloride hemihydrate was prepared using the anhydrous (R)-8-chloro-1-methyl-2,3,4,5-tetrahydro-1H-3-benzazepine hydrochloride in the presence of isopropanol, water and cyclohexane under an atmosphere of nitrogen.

It has now been discovered that (R)-8-chloro-1-methyl-2,3,4,5-tetrahydro-1H-benzo[d]azepinium hemitartrate can be converted directly to (R)-8-chloro-1-methyl-2,3,4,5-tetrahydro-1H-3-benzazepine hydrochloride hemihydrate without isolation of the free base and without formation of the anhydrous (R)-8-chloro-1-methyl-2,3,4,5-tetrahydro-1H-3-benzazepine HCl salt.

In general, (R)-8-chloro-1-methyl-2,3,4,5-tetrahydro-1H-3-benzazepine hydrochloride hemihydrate is prepared comprising the steps:

1) neutralizing the (R)-8-chloro-1-methyl-2,3,4,5-tetrahydro-1H-benzo[d]azepinium hemitartrate to form the free base (R)-8-chloro-1-methyl-2,3,4,5-tetrahydro-1H-3-benzazepine;

2) contacting the free base (R)-8-chloro-1-methyl-2,3,4,5-tetrahydro-1H-3-benzazepine with HCl in the presence of water to form (R)-8-chloro-1-methyl-2,3,4,5-tetrahydro-1H-3-benzazepine hydrochloride; and 3) crystallizing the (R)-8-chloro-1-methyl-2,3,4,5-tetrahydro-1H-3-benzazepine hydrochloride to form (R)-8-chloro-1-methyl-2,3,4,5-tetrahydro-1H-3-benzazepine hydrochloride hemihydrate.

One base that is particularly useful in neutralizing the hemitartrate salt is aqueous potassium carbonate. In contrast, it was found that when aqueous NaOH was used to neutralize (R)-8-chloro-1-methyl-2,3,4,5-tetrahydro-1H-benzo[d]azepinium hemitartrate a difficult-to-separate emulsion was generated. However, aqueous potassium carbonate can be used that is essentially free of any emulsion when extracting the free base (R)-8-chloro-1-methyl-2,3,4,5-tetrahydro-1H-3-benzazepine after neutralizing. In addition, it was also found that ethyl acetate was particularly suitable for use in the steps of neutralizing, contacting and crystallizing to provide (R)-8-chloro-1-methyl-2,3,4,5-tetrahydro-1H-3-benzazepine hydrochloride hemihydrate. Ethyl acetate was also found particularly useful for the dissolution of concentrations of water appropriate for crystallizing the (R)-8-chloro-1-methyl-2,3,4,5-tetrahydro-1H-3-benzazepine hydrochloride hemihydrate.

Some embodiments of the present invention provide methods for preparing (R)-8-chloro-1-methyl-2,3,4,5-tetrahydro-1H-3-benzazepine HCl hemihydrate of Formula (II):

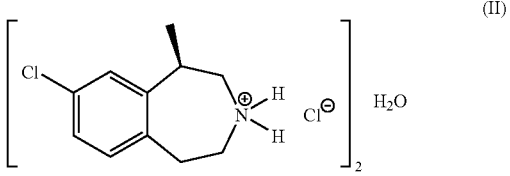

(II)

comprising the steps:

neutralizing 8-chloro-1-methyl-2,3,4,5-tetrahydro-1H-benzoazepinium hemitartrate of the formula:

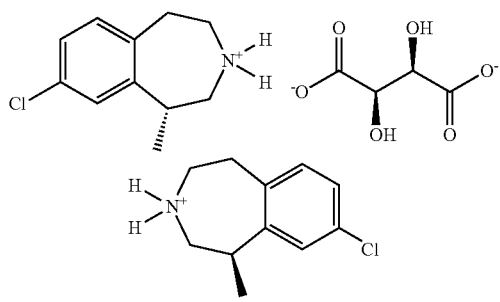

with potassium carbonate in the presence of water and ethyl acetate to form a biphasic liquid mixture consisting essentially of an aqueous phase and an ethyl acetate phase comprising (R)-8-chloro-1-methyl-2,3,4,5-tetrahydro-1H-3-benzazepine of Formula (Ia):

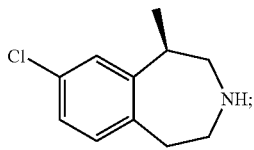

separating the ethyl acetate phase of the biphasic liquid mixture from the aqueous phase of the biphasic liquid mixture;

contacting the ethyl acetate phase with HCl in the presence of water to form an HCl salt of (R)-8-chloro-1-methyl-2,3,4,5-tetrahydro-1H-3-benzazepine, wherein the ratio of water to (R)-8-chloro-1-methyl-2,3,4,5-tetrahydro-1H-3-benzazepine is at least 1 to 2; and crystallizing the HCl salt of (R)-8-chloro-1-methyl-2,3,4,5-tetrahydro-1H-3-benzazepine to form (R)-8-chloro-1-methyl-2,3,4,5-tetrahydro-1H-3-benzazepine HCl hemihydrate.

In some embodiments, crystallizing the HCl salt of (R)-8-chloro-1-methyl-2,3,4,5-tetrahydro-1H-3-benzazepine formed substantially pure (R)-8-chloro-1-methyl-2,3,4,5-tetrahydro-1H-3-benzazepine HCl hemihydrate.

Some embodiments of the present invention provide methods for preparing (R)-8-chloro-1-methyl-2,3,4,5-tetrahydro-1H-3-benzazepine HCl hemihydrate of Formula (II) wherein the water in the contacting step is substantially dissolved in the ethyl acetate phase.

In some embodiments, the water in the ethyl acetate phase is present in an amount of about 0.2% to about 2% by weight.

In some embodiments, the water in the ethyl acetate phase is present in an amount of about 0.2% to about 1% by weight.

In some embodiments, the water in the ethyl acetate phase is present in an amount of about 0.4% to 0.8% by weight.

In some embodiments, the water in the ethyl acetate phase is present in an amount of about 0.6% by weight.

Some embodiments of the present invention provide methods for preparing (R)-8-chloro-1-methyl-2,3,4,5-tetrahydro-1H-3-benzazepine HCl hemihydrate of Formula (II) wherein the biphasic liquid mixture is substantially emulsion-free.

Some embodiments of the present invention provide methods for preparing (R)-8-chloro-1-methyl-2,3,4,5-tetrahydro-1H-3-benzazepine HCl hemihydrate of Formula (II) wherein the contacting step is carried out at a temperature of about 0° C. to about 25° C.

Some embodiments of the present invention provide methods for preparing (R)-8-chloro-1-methyl-2,3,4,5-tetrahydro-1H-3-benzazepine HCl hemihydrate of Formula (II) wherein the HCl in the contacting step is in the form of a gas.

In some embodiments, (R)-8-chloro-1-methyl-2,3,4,5-tetrahydro-1H-3-benzazepine hydrochloride hemihydrate is isolated with an achiral purity of about 99% or greater.

In some embodiments, (R)-8-chloro-1-methyl-2,3,4,5-tetrahydro-1H-3-benzazepine hydrochloride hemihydrate is isolated with a chiral purity of about 99% or greater.

IPC: Water content of ethyl acetate layer <0.8%. This stage is depicted in Synthetic Scheme 1.5.

Synthetic Scheme 1.5

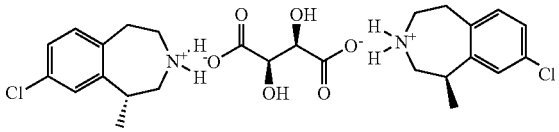

(R)-8-Chloro-1-methyl-2,3,4,5-tetrahydro-1H-benzo[d]azepinium
Hemitartrate Final Isolated Intermediate;
$C_{26}H_{34}Cl_2N_2O_6$ Mol. Wt.: 541.46 i) $K_2CO_3$, $H_2O$
ii) Ethyl acetate  Stage 7
iii) HCl gas

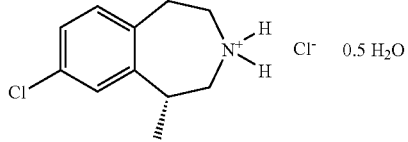

(R)-8-Chloro-1-methyl-2,3,4,5-tetrahydro-1H-benzo[d] azepine
Hemihydrate
$C_{11}H_{15}Cl_2N$. 0.5 $H_2O$
Mol. Wt.: 241.16

In summary, the (R)-8-chloro-1-methyl-2,3,4,5-tetrahydro-1H-3-benzazepine hemihydrate process involves four chemical reactions and four purification operations. In Stage 4, [2-(4-chloro-phenyl)-ethyl]-(2-chloro-propyl)-ammonium chloride was used to form the backbone of the molecule resulting in a crude product containing 35-40% of the desired enantiomer, (R)-8-chloro-1-methyl-2,3,4,5-tetrahydro-1H-3-benzazepine (free base). During Stage 5 and 6, the tartaric acid resolution and successive purification operations, which involve two crystallizations of the hemitartrate, afford a highly pure final intermediate, (R)-8-chloro-1-methyl-2,3,4,5-tetrahydro-1H-benzo[d]azepinium Hemitartrate. In Stage 7, (R)-8-chloro-1-methyl-2,3,4,5-tetrahydro-1H-benzo[d]azepinium Hemitartrate was converted to a higher purity. The highly selective resolution using L-(+)-tartaric acid and successive crystallizations are the critical steps that afford high purity of the (R)-8-chloro-1-methyl-2,3,4,5-tetrahydro-1H-3-benzazepine.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Conversion of 2-(4'-Chlorophenyl)ethanol to 2-(4'-chlorophenyl)ethyl Bromide

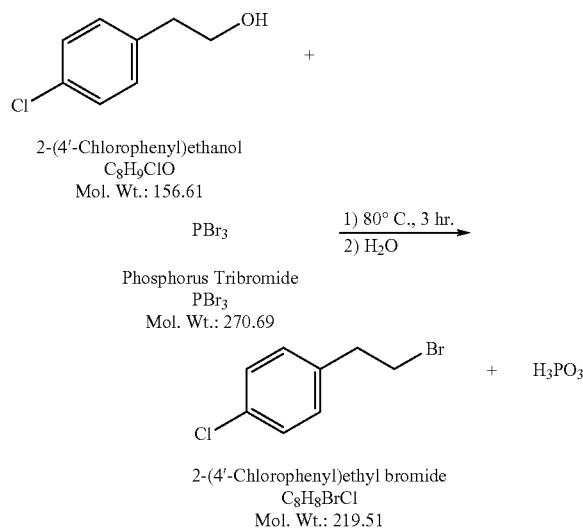

Raw Materials and Yield

| 1.00 Kg | 6.39 moles | 2-(4'-Chlorophenyl)ethanol (Starting Material) |
| 0.869 Kg | 3.21 moles | Phosphorous Tribromide |
| 0.599 Kg | | Purified Water |
| 1.33 Kg | 6.06 moles 94.9% yield | 2-(4'-Chlorophenyl)ethyl Bromide (Product, assay corrected) |

Volume Efficiency

The volume efficiency was 1.76 L per Kg of 2-(4'-chlorophenyl)ethanol starting material or 758 g of 2-(4'-chlorophenyl) ethyl bromide product (assay corrected) per liter.

Process Description

To a reactor affixed with a vent to a caustic scrubber to capture HBr gas that might evolve during the reaction was added 2-(4'-chlorophenyl)ethanol (1.00 Kg, 6.39 moles, 1.00 equiv.). The reactor contents were cooled to 0° C. The feed pump and line were rinsed with cyclohexane (0.019 Kg), and the rinses were directed to waste disposal. To the cooled solution was added phosphorous tribromide (0.869 Kg, 3.21 moles, 0.503 equiv.) while the stirred reactor contents were maintained at 0-10° C. The resulting reaction was highly exothermic and was controlled by the addition rate with a jacket temperature of −5° C. to −10° C. The feed pump and line was rinsed with cyclohexane (0.019 Kg), and the rinses were directed to waste disposal. The resulting reaction mixture was heated to 25° C. (20° C. to 30° C.), and stirring was continued at this temperature for 2 hours (1 to 3 hours). After this time, the reaction mixture was slowly heated to 80° C. (75 to 85° C.) over 60 minutes (45 to 75 minutes), and stirring at that temperature was continued for 3 hours (2 to 4 hours). A slightly turbid emulsion was formed upon heating. The reactor contents were cooled to 22° C. and then a sample of the reaction mixture was analyzed for reaction completion (>99% by HPLC peak area). The reaction mixture was a thick but easily stirred emulsion. A receiver vented to a caustic scrubber was charged with purified water (0.514 Kg). The receiver contents were cooled to 5-20° C. The reaction mixture was transferred from the reactor to the receiver at a rate sufficiently slow to maintain the stirred receiver contents at about 15° C. The receiver contents were warmed to 35-40° C. and filtered through a polishing filter. The reactor was washed with additional purified water (0.085 Kg), and the washings were passed through the filter into the aqueous product mixture. The phases were allowed to separate at 35-40° C. The lower phase was drained from the upper phase. The lower phase weighed about 1.39 Kg and was about 96% pure 2-(4'-chlorophenyl)ethyl bromide, which was therefore obtained in about 94.9% yield (assay corrected).

Example 2

Conversion of 2-(4'-Chlorophenyl)ethyl Bromide to [2-(4-Chloro-phenyl)-ethyl]-(2-chloro-propyl)-ammonium chloride

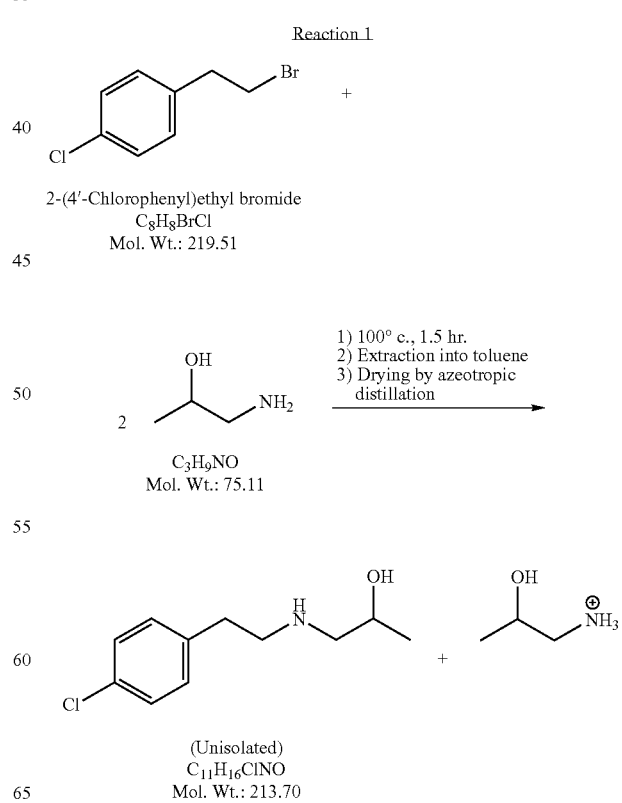

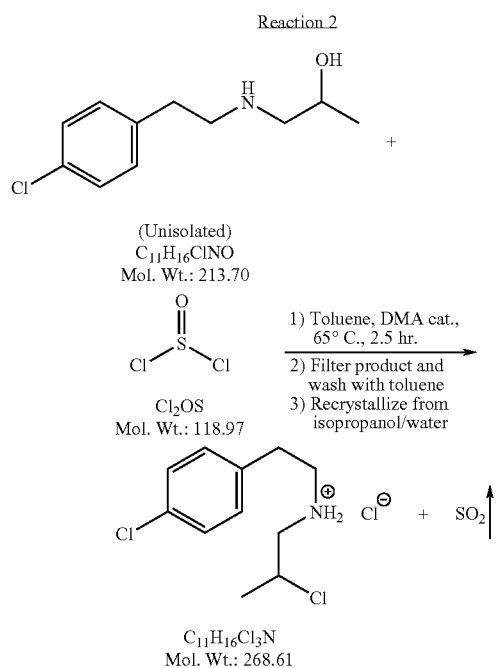

Reaction 2

(Unisolated)
C₁₁H₁₆ClNO
Mol. Wt.: 213.70

Cl₂OS
Mol. Wt.: 118.97

1) Toluene, DMA cat., 65° C., 2.5 hr.
2) Filter product and wash with toluene
3) Recrystallize from isopropanol/water $C_{11}H_{16}Cl_3N$
Mol. Wt.: 268.61

Raw Materials and Yield

| | | |
|---|---|---|
| 1.71 Kg | 22.8 moles | 1-Amino-2-propanol |
| 1.00 Kg | 4.56 moles | 2-(4'-Chlorophenyl)ethyl Bromide (Starting Material, not corrected for assay) |
| 8.40 Kg | | Toluene |
| 1.16 Kg | | Purified Water |
| 0.119 Kg | 1.37 moles | N,N-Dimethylacetamide (DMA) |
| 0.690 Kg | 5.80 moles | Thionyl chloride |
| 3.31 Kg | | Isopropanol |
| 0.865 Kg | 3.22 moles | [2-(4-Chloro-phenyl)-ethyl]-(2-chloro-propyl)-ammonium chloride |
| | 70.7% yield | (Product, not corrected for assay) |

Volume Efficiency

The volume efficiency was 6.5 L per Kg of 2-(4'-chlorophenyl)ethyl bromide starting material (not corrected for assay) or 133 g of [2-(4-Chloro-phenyl)-ethyl]-(2-chloropropyl)-ammonium chloride product (not corrected for assay) per liter.

Process Description

Reaction 1: Conversion of 2-(4'-Chlorophenyl)ethyl Bromide to 1-[2-(4-Chloro-phenyl)-ethylamino]-propan-2-ol To a reactor was charged 1-amino-2-propanol (1.71 Kg, 22.8 moles, 5.00 equiv.). The reactor contents were heated to 85-90° C. The feed pump and line were rinsed with toluene (0.50 Kg), and the rinse was directed to waste disposal. To the reactor was added 2-(4'-chlorophenyl)ethyl bromide (1.00 Kg, 4.56 moles, 1.00 equiv. not corrected for assay) over 45 minutes while the stirred reactor contents were maintained at ≦100° C. The feed pump and line were rinsed with toluene (0.50 Kg), and the rinses were directed to waste disposal. The reaction mixture was stirred at 85-100° C. for 90 minutes and then cooled to 50° C. A sample of the reaction mixture was removed to verify reaction completion (>98%) by HPLC. Purified water was added (1.0 Kg) while the stirred reactor contents were maintained at 70-75° C. While the stirred reactor contents continued to be maintained at 70-75° C., toluene was added (1.8 Kg). Stirring was maintained at that temperature for 20 minutes and then stopped to allow the layers to separate for 15 minutes. The lower aqueous layer at 70-75° C. was drained and extracted with additional toluene; either a single 1.6-Kg portion or two 0.52-Kg portions can be used. Toluene (1.0 Kg) was removed from the combined organic phases by vacuum distillation at 40-60° C. and 80-100 mbar. The distillation residue's water content was verified by Karl Fischer analysis to be <0.15%. If not, then more toluene was charged to the product mixture, and the vacuum distillation was continued until the Karl Fischer analysis was <0.15%.

Reaction 2: Conversion of 1-[2-(4-Chloro-phenyl)-ethylamino]-propan-2-ol to [2-(4-Chloro-phenyl)-ethyl]-(2-chloro-propyl)-ammonium Chloride To the stirred reactor contents at 42° C. was added N,N-dimethylacetamide (DMA, 0.119 Kg, 1.37 moles, 0.30 equiv.) followed by toluene (1.6 Kg). The reactor vent was connected to a caustic scrubber to capture the sulfur dioxide and HCl gases evolved during the subsequent steps. The reactor contents were heated to 55° C. and then charged with thionyl chloride (0.690 Kg, 5.80 moles, 1.273 equiv.) at a rate sufficiently slow to maintain the stirred reactor contents at 50-60° C. During the addition, a suspension was formed and progressively thickened but remained stirrable. The feed line was rinsed into the reactor with toluene (1.0 Kg). Process volume peaked at this point at 6.5 L. The thick reaction slurry was stirred at 60-65° C. for 2-3 hours and then cooled to 17° C. A sample of the reaction mixture was obtained to determine reaction completion by HPLC. (Conversion was typically >99% by HPLC peak area.) The suspension was filtered. The reactor and the filtered solid product were washed with toluene (2.4 Kg). The resulting brown crude solid product was reslurried in a mixture of isopropanol (1.47 Kg) and purified water (0.157 Kg). The stirred slurry was heated to reflux (80-85° C.) for 0.5-1.0 hour. The resulting clear brown solution was cooled to 12° C. over 1.5 hours and stirring was continued at that temperature for another 1.5 hours. The resulting slurry was further cooled to 2° C. over 1.5 hours and stirring was continued at that temperature for another 1.5 hours. The product was isolated in a filter or a centrifuge at 2° C. The reactor and the wet cake were washed with isopropanol in several portions (up to five, 1.84 Kg total). The off-white to light beige wet product was dried under vacuum at 70° C. and 30 mbar. The isolated yield of [2-(4-chloro-phenyl)-ethyl]-(2-chloro-propyl)-ammonium chloride from 2-(4'-chlorophenyl)ethyl bromide in the telescoped process was 0.865 Kg (70.7%, not corrected for assay).

Variation of Reactions 1 and 2

After the aqueous phase from Reaction 1 was extracted a second time with additional toluene (1.60 Kg) at 70-75° C., toluene (1.80 kg) was distilled off the combined organic phases at 40°-60° C. and 80-100 mbar. Make-up toluene (1.80 kg) was added to the distillation residue, and the water content of the resulting solution was verified to be <0.15% by Karl Fischer analysis. If the water content were ≧0.15%, then distillative removal of toluene (1.8 kg) and addition of fresh toluene (1.8 kg) would be repeated until it is <0.15%. Reaction 2 was then executed without adding any more toluene. After reaction conversion had been determined to be >99% by HPLC peak area, the reaction mixture was cooled to 0-5° C. 2-Propanol (1.06 kg) was then added sufficiently slowly to maintain the stirred reactor contents at 0-5° C. The addition was initially endothermic, but within two minutes, reaction of thionyl chloride became strongly exothermic (191 W/kg). The resulting mixture was stirred at 0-5° C. for an additional 1.5-2.5 hours to complete product precipitation and quenching of excess thionyl chloride. The solid product was then isolated by filtration. The reactor and then the product cake were washed thoroughly with three 1.00 kg-portions of cold 2-propanol. The washed product cake was vacuum dried at 80-85° C. and 30 mbar to provide colorless to beige [2-(4-chloro-phenyl)-ethyl]-(2-chloro-propyl)-ammonium chloride (0.916 kg, 74.9% yield from 2-(4'-chlorophenyl)ethyl bromide uncorrected for assay).

Example 3

Conversion of [2-(4-Chloro-phenyl)-ethyl]-(2-chloro-propyl)-ammonium Chloride to 8-Chloro-1-methyl-2,3,4,5-tetrahydro-1H-benzo[d]azepinium Hemitartrate

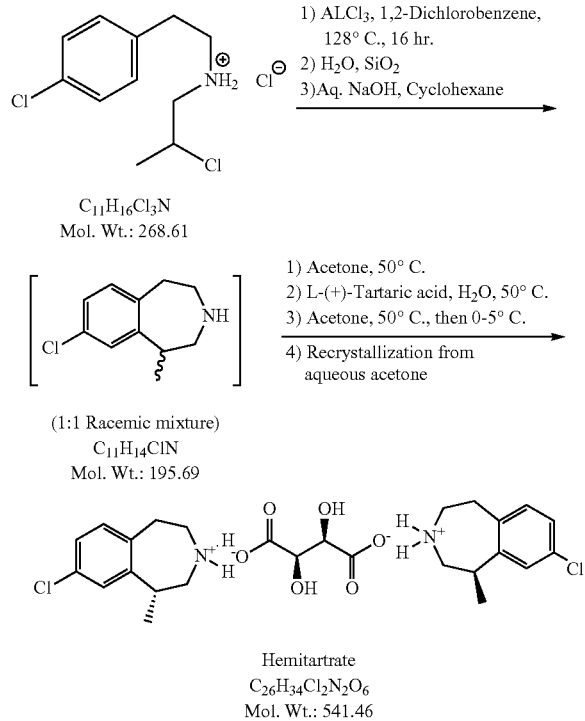

Raw Materials and Yield

| 1.00 Kg | 3.72 mol | [2-(4-Chloro-phenyl)-ethyl]-(2-chloro-propyl)-ammonium chloride (Starting Material) |
| --- | --- | --- |
| 0.745 Kg | 5.58 mol | Aluminum Chloride |
| 4.04 Kg | 30.3 mol | 30% NaOH Solution |
| 0.122 Kg | 0.815 mol | L-Tartaric Acid |
| 0.160 Kg | | Silica Gel 60, 63-200 μm |
| 5.63 Kg | | Purified Water |
| 2.88 Kg | | 1,2-Dichlorobenzene |
| 1.10 Kg | | Cyclohexane |
| 5.49 Kg | | Acetone |

| 0.80 g | | 8-Chloro-1-methyl-2,3,4,5-tetrahydro-1H-benzo[d]azepinium Hemitartrate Seed Crystals |
| --- | --- | --- |
| 0.273 Kg | 0.504 mol[1] | 8-Chloro-1-methyl-2,3,4,5-tetrahydro-1H-benzo[d]azepinium |
| | 27.1% yield[2] | Hemitartrate (Product, assay corrected) |

[1]Based on the 8-Chloro-1-methyl-2,3,4,5-tetrahydro-1H-benzo[d]azepinium Hemitartrate molecular formula that incorporates two 8-chloro-1-methyl-2,3,4,5-tetrahydro-1H-3-benzazepine ammonium cations and that has molecular weight 541.46.
[2]Based on one mole of [2-(4-Chloro-phenyl)-ethyl]-(2-chloro-propyl)-ammonium chloride starting material (m.w. 268.61) being able to produce a theoretical maximum of one-half mole of 8-chloro-1-methyl-2,3,4,5-tetrahydro-1H-benzo[d]azepinium Hemitartrate product of mol. wt. 541.46.

Volume Efficiency

The volume efficiency was 5.68 L per Kg of [2-(4-Chloro-phenyl)-ethyl]-(2-chloro-propyl)-ammonium chloride starting material (not corrected for assay) or 46.7 g of 8-chloro-1-methyl-2,3,4,5-tetrahydro-1H-benzo[d]azepinium hemitartrate product (corrected for assay) per liter.

Process Description

Conversion of [2-(4-Chloro-phenyl)-ethyl]-(2-chloro-propyl)-ammonium Chloride to 8-Chloro-1-methyl-2,3,4,5-tetrahydro-1H-benzazepine To a reactor equipped with overhead agitation, jacket temperature control, a nitrogen inlet, and a caustic scrubber vent were charged, in the specified order, [2-(4-chloro-phenyl)-ethyl]-(2-chloro-propyl)-ammonium chloride (1.00 Kg, 3.72 mol, 1.00 equiv.), aluminum chloride (0.745 Kg, 5.58 mol, 1.50 equiv.), and 1,2-dichlorobenzene (2.88 Kg). The stirred reactor contents were heated to 125-130° C., and stirring was continued at that temperature for 14-18 hours. At 60-70° C., a dark colored solution was obtained. After reaction completion (<1.0% starting material by HPLC peak area) had been verified, the stirred reactor contents were cooled to 30-35° C. To a second reactor vented to a caustic scrubber was charged purified water (1.60 L) and silica gel (0.160 Kg). The Friedel Crafts reaction mixture was transferred from the first reactor to the second reactor sufficiently slowly to maintain the stirred contents of the second reactor at <60° C. After the transfer is completed, the next step may be executed without any hold period. The silica gel was filtered on a medium to coarse filter element at 55-60° C., and the filtered solids were subsequently washed with purified water (800 mL) preheated to 50-60° C. The combined mother and wash liquor filtrates were cooled to 20-25° C. with vigorous agitation. Then the stirring was stopped, and the phases were allowed to separate at 20-25° C. (Process volume peaked at this point at 5.68 L). Three phases separated after 1-2 hours of standing. The lowest layer was drained to waste disposal. This dark layer consisted mostly of 1,2-dichlorobenzene (1.64 Kg, 1.33 L) at pH 34. About 1% of the product was lost to this layer. The remaining two phases were allowed to stand without agitation for another 24 hours. The lower layer was drained and saved (Layer A). This light colored phase (2.64 Kg, 2.00 L, pH 2-3) contains ~90% 8-chloro-1-methyl-2,3,4,5-tetrahydro-1H-benzazepine. The upper layer (2.24 Kg of a turbid water phase at pH 0-1) contains ~14% 8-chloro-1-methyl-2,3,4,5-tetrahydro-1H-benzazepine and remained in the reactor for back-extraction. The reactor was charged with cyclohexane (1.10 Kg) and then 30% aqueous NaOH (2.44 Kg, 18.3 mol, 4.91 equiv.). The resulting mixture (5.60 L) was stirred vigorously for 30 minutes at room temperature. The stirring was stopped, and the phases were allowed to separate for 2540 minutes. If the pH of the lower (aqueous) phase was ≧13, it was drained to waste disposal. Otherwise, more 30% aqueous NaOH was added, and this extraction was repeated. At pH 14, the aqueous phase contains <0.1% 8-chloro-1-methyl-2,3,4,5-tetrahydro-1H-benzazepine free base. The remaining upper (organic) phase from the reactor was drained and saved (Layer B). The reactor was rinsed with purified water and followed by a suitable organic solvent to remove residual salts. The lower, light-colored product phase (the middle of the original three phases, Layer A) and the upper phase (organic, Layer B) were returned to the reactor. To the stirred reactor contents was added 30% aqueous NaOH (1.60 Kg, 12.0 mol, 3.23 equiv.). The reactor contents were stirred vigorously for 0.5 hours. The stirring was discontinued and the phases were allowed to separate over 15-30 minutes. The lower (aqueous) layer was drained to waste disposal. To the upper (organic) phase remaining in the reactor was added purified water (2.40 Kg). The reactor contents were stirred vigorously at 60-65° C. for 0.5 hours. The stirring was discontinued, and the phases were allowed to separate at 60-65° C. over 1.5-2 hours. The lower (aqueous) layer was drained to waste disposal. With a reactor jacket temperature of 55-60° C., solvent from the upper (organic) layer was removed by vacuum distillation at pressures starting at 115-152 torr and falling to 40 torr. The crude product, 8-chloro-1-methyl-2,3,4,5-tetrahydro-1H-benzazepine as the free base, was obtained as a yellow to brown oil distillation residue.

Resolution of 8-Chloro-1-methyl-2,3,4,5-tetrahydro-1H-benzazepine to 8-Chloro-1-methyl-2,3,4,5-tetrahydro-1H-benzo[d]azepinium Hemitartrate The distillation residue (crude 8-chloro-1-methyl-2,3,4,5-tetrahydro-1H-benzazepine as the free base) was dissolved in acetone (0.400 Kg). The resulting solution was drained and weighed to assay the 8-chloro-1-methyl-2,3,4,5-tetrahydro-1H-benzazepine content by HPLC. Results of the assay were used to calculate charges of acetone, L-tartaric acid, and water. The quantities indicated below are typical for achievement of the target 8-chloro-1-methyl-2,3,4,5-tetrahydro-1H-benzazepine:acetone:L-tartaric acid:water mole ratio of 1.00: 9.6:0.25:3.6 prior to addition of seed crystals. More acetone (1.415 Kg) was added to the reactor and the stirred reactor contents were heated to 47-52° C. To the resulting solution was added a solution of L-tartaric acid (0.1223 Kg, 0.815 mol, 0.219 equiv.) in purified water (0.211 Kg) at a steady rate over 5-15 minutes. A thin suspension formed during the addition but then redissolved when the mixture temperature was reestablished at 50° C. Hemitartrate seed crystals (0.80 g) were added to the 50° C. solution to achieve cloudiness and to initiate nucleation. Nucleation was allowed to continue for 2-3 hours with agitation at 47-52° C. Acetone (0.473 Kg) was added to the reactor while the stirred reactor contents were maintained at 50° C. The resulting suspension was cooled to 0-5° C. slowly over 3-5 hours. Stirring was continued at 0° C. for another 1-3 hours. The resulting white precipitate was collected on a medium to fine filter element and then washed with a mixture of acetone (0.900 Kg) and purified water (0.054 Kg). The enantiomeric excess (ee) of the wet cake was determined.

If the ee was <98%, the wet cake was transferred back into the reactor and reslurried in a mixture of acetone (1.90 Kg) and purified water (0.400 Kg) at 55-60° C. for 0.5-1 hour. If dissolution bad not been achieved after one hour, then water (approximately 0.160 Kg) was added until a clear solution was achieved. The resulting mixture was then cooled to 0-5° C. slowly over 2-3 hours. Stirring at 0° C. was continued for another 3-5 hours. The resulting white precipitate was collected on a medium to fine filter element and then washed with acetone (0.400 Kg) at 0-4° C.

The washed solid product (296 g wet) was dried at 60-65° C. under full vacuum for 15-20 hours. The yield of 8-chloro-1-methyl-2,3,4,5-tetrahydro-1H-benzo[d]azepinium hemitartrate, with about 99.7% ee and 7.5 wt. % water content, was 295 g (27.1% based on racemic [2-(4-chloro-phenyl)-ethyl]-(2-chloro-propyl)-ammonium chloride and corrected for product water content).

Example 4

Conversion of 8-Chloro-1-methyl-2,3,4,5-tetrahydro-1H-benzo[d]azepinium Hemitartrate to (R)-8-Chloro-1-methyl-2,3,4,5-tetrahydro-1H-3-benzazepine Hemihydrate

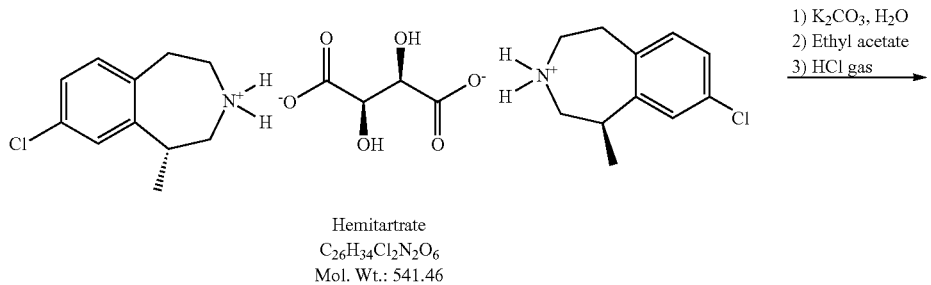

Hemitartrate
$C_{26}H_{34}Cl_2N_2O_6$
Mol. Wt.: 541.46

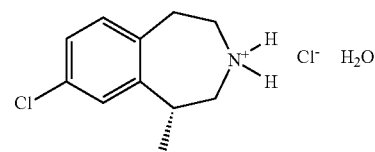

2

Hemihydrate
$C_{11}H_{15}Cl_2N \cdot 0.5\ H_2O$
Mol. Wt.: 241.16

Raw Materials and Yield

| | | |
|---|---|---|
| 1.00 Kg | 1.71 mol[1] | 8-Chloro-1-methyl-2,3,4,5-tetrahydro-1H-benzo[d]azepinium hemitartrate (Starting Material) |
| 0.508 Kg | 3.68 mol | Potassium Carbonate |
| 5.40 Kg | | Purified Water |
| 10.2 Kg | | Ethyl Acetate |
| 0.127 Kg | 3.47 mol | Hydrogen Chloride Gas |
| 1.33 g | | (R)-8-Chloro-1-methyl-2,3,4,5-tetrahydro-1H-3-benzazepine hemihydrate Seed Crystals |
| 0.741 Kg | 3.07 mol | (R)-8-Chloro-1-methyl-2,3,4,5-tetrahydro-1H-3-benzazepine |
| | 89.9% yield[2] | hemihydrate (Product, not corrected for assay) |

[1] Based on the 8-chloro-1-methyl-2,3,4,5-tetrahydro-1H-benzo[d]azepinium hemitartrate molecular formula that incorporates two 8-chloro-1-methyl-2,3,4,5-tetrahydro-1H-benzazepine ammonium cations and that has molecular weight 541.46. The moles are corrected for assay, but the weight was not.
[2] Based on one mole of 8-chloro-1-methyl-2,3,4,5-tetrahydro-1H-benzo[d]azepinium hemitartrate starting material of mol. wt. 541.46 being able to produce a theoretical maximum of two moles of (R)-8-chloro-1-methyl-2,3,4,5-tetrahydro-1H-3-benzazepine hemihydrate product (m.w. 241.16).

Volume Efficiency

The volume efficiency was 6.91 L per Kg of 8-chloro-1-methyl-2,3,4,5-tetrahydro-1H-benzo[d]azepinium hemitartrate starting material (not corrected for assay) or 107 g of (R)-8-chloro-1-methyl-2,3,4,5-tetrahydro-1H-3-benzazepine hemihydrate product (not corrected for assay) per liter.

Process Description

To a reactor equipped with overhead agitation and a nitrogen inlet was charged, in the specified order, 8-chloro-1-methyl-2,3,4,5-tetrahydro-1H-benzo[d]azepinium hemitartrate (1.00 Kg containing 7.5 wt % water, 1.71 mol, 0.500 equiv.), potassium carbonate (0.508 Kg, 3.68 moles, 1.076 equiv.), ethyl acetate (2.68 Kg), and purified water (2.68 Kg). The resulting mixture was stirred at 20-25° C. for 3040 minutes, and then the phases were allowed to separate over 0.5-1 hour. The lower (aqueous) phase was drained to waste disposal. Purified water (2.68 Kg) was added to the reactor, and the resulting mixture was vigorously stirred for 10-20 minutes. The phases were allowed to separate over 1-1.5 hour. The lower (aqueous) phase was drained to waste disposal. With the reactor contents at a temperature of 40-45° C., the solvent was removed by vacuum distillation at pressures falling from 153 torr to 46 torr. The residue was cooled to 20-25° C. Ethyl acetate (3.81 Kg) was charged to the reactor, and the distillation residue was dissolved with stirring. The water content of the resulting solution was verified by Karl Fischer analysis to be <0.8 wt. %. The solution was filtered through a polishing filter. The reactor was rinsed through the filter with ethyl acetate (2.33 Kg) previously verified by Karl Fischer analysis to have <0.05 wt. % water content. Both the solution and rinse filtrates were charged back into the reactor. Purified water (39.9 g) was added to the reactor. The stirred reactor contents were cooled to 0-5° C., and then HCl gas (19.0 g, 0.521 mol, 0.153 equiv.) was added while the stirred reactor contents were maintained at 0-5° C. (R)-8-chloro-1-methyl-2,3,4,5-tetrahydro-1H-3-benzazepine hemihydrate seed crystals (1.33 g) were added to the stirred reactor contents to initiate nucleation at 0-5° C. The remaining HCl gas (107.6 g, 2.95 mol, 0.864 equiv.) was charged to the reactor at a steady rate over at least 1.5-2 hours while the stirred reactor contents were maintained at 0-5° C. The resulting suspension was stirred at 0-5° C. for 2 hours. The resulting white precipitate was collected on a medium to fine filter element. The reactor and then the filtered solid product were washed with ethyl acetate (1.33 Kg). The wet cake (ca. 867 g) was dried at full vacuum and 33-37° C. for 20 hours or until the cake temperature had been stable for 4 hours, whichever occurred first. The resulting (R)-8-chloro-1-methyl-2,3,4,5-tetrahydro-1H-3-benzazepine hemihydrate (3.7 wt. % water content, 14.7% chloride content, <0.01% ROI, >99.6% ee, >99% HPLC purity, and <0.1% wrong isomer content) was obtained in a yield of about 741 g (89.9%).

Various modifications of the invention, in addition to those described herein, will be apparent to those skilled in the art from the foregoing description. Such modifications are also intended to fall within the scope of the appended claims.

What is claimed is:

1. A method for preparing a compound of Formula (I):

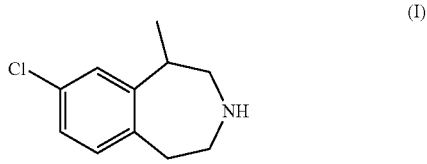

comprising the steps:
reacting [2-(4-chloro-phenyl)-ethyl]-(2-chloro-propyl)-ammonium chloride with AlCl$_3$ in the presence of 1,2-dichlorobenzene at a temperature of about 120° C. to about 135° C. for about 14 hours to about 18 hours under conditions suitable for forming a crude reaction mixture comprising said compound of Formula (I);
contacting said crude reaction mixture with silica gel and water to form a suspension;
filtering said suspension to form a triphasic liquid mixture; and
isolating said compound of Formula (I) from said triphasic liquid mixture.

2. The method according to claim 1, further comprising the steps:
separating the top phase and the middle phase from the bottom phase of said triphasic liquid mixture; and
isolating said compound of Formula (I) from the top phase and the middle phase.

3. The method according to claim 2, wherein the bottom phase of said triphasic liquid mixture comprises 1,2-dichlorobenzene.

4. The method according to claim 3, wherein the middle phase of said triphasic liquid mixture contains said compound of Formula (I) in an amount greater than the amount of said compound of Formula (I) contained in the top phase or the bottom phase of said triphasic liquid mixture.

5. The method according to claim 4, wherein the middle phase of said triphasic liquid mixture contains said compound of Formula (I) in an amount of about 80% or greater.

6. The method according to claim 5, wherein said isolating step further comprises the steps:
separating the top phase from the middle phase;
extracting said compound of Formula (I) from the top phase with an extracting solvent and separating said extracting solvent comprising said compound of Formula (I) from the top phase;
combining said extracting solvent comprising said compound of Formula (I) together with the middle phase to form a combined mixture;
washing said combined mixture with a basic, aqueous solution and separating said basic, aqueous solution from said combined mixture to form a washed, combined solution; and concentrating said washed, combined solution to provide said compound of Formula (I).

7. The method according to claim 6, wherein said basic solution is aqueous sodium hydroxide.

8. The method according to claim 7, wherein said extracting solvent is cyclohexane.

9. The method according to claim 8, wherein said [2-(4-chloro-phenyl)-ethyl]-(2-chloro-propyl)-ammonium chloride is prepared by the method comprising reacting 1-[2-(4-chloro-phenyl)-ethylamino]-propan-2-ol and thionyl chloride for a time and under conditions suitable for forming said [2-(4-chloro-phenyl)-ethyl]-(2-chloropropyl-ammonium chloride.

10. The method according to claim 9, further comprising the steps:
determining that said 1-[2-(4-chloro-phenyl)-ethylamino]-propan-2-ol is substantially converted to said [2-(4-chloro-phenyl)-ethyl]-(2-chloro-propyl)-ammonium chloride; and in a subsequent step
quenching any residual amount of said thionyl chloride with a $C_{1-6}$ alcohol.

11. The method according to claim 10, wherein said $C_{1-6}$ alcohol is isopropanol.

12. The method according to claim 11, wherein said 1-[2-(4-chloro-phenyl)-ethylamino]-propan-2-ol is prepared by the method comprising reacting 2-(4'-chlorophenyl)ethyl bromide and 1-amino-2-propanol for a time and under conditions suitable for forming an alkylation mixture comprising said 1-[2-(4-chloro-phenyl)-ethylamino]-propan-2-ol.

13. The method according to claim 12, further comprising the steps:
mixing said alkylation mixture comprising said 1-[2-(4-chloro-phenyl)-ethylamino]-propan-2-ol and water to form a biphasic mixture;
extracting said 1-[2-(4-chloro-phenyl)-ethylamino]-propan-2-ol from said biphasic mixture with an extracting solvent comprising toluene to form a new biphasic mixture consisting essentially of an aqueous lower phase and an upper phase comprising toluene and said 1-[2-(4-chloro-phenyl)-ethylamino]-propan-2-ol;
separating said upper phase comprising toluene and said 1-[2-(4-chloro-phenyl)ethylamino]-propan-2-ol from said aqueous lower phase; and
removing water from said upper phase comprising toluene and said 1-[2-(4-chlorophenyl)-ethylamino]-propan-2-ol by azeotropic distillation to form a solution comprising toluene and 1-[2-(4-chloro-phenyl)-ethylamino]-propan-2-ol.

14. The method according to claim 13, wherein said solution comprising toluene and 1-[2-(4-chloro-phenyl)-ethylamino]-propan-2-ol contains about 0.5% water or less.

15. The method according to claim 14, wherein said 2-(4'-chlorophenyl)ethyl bromide is prepared by the method comprising reacting 2-(4'-chlorophenyl)ethanol with phosphorous tribromide for a time and under conditions suitable for forming said 2-(4'-chlorophenyl)ethyl bromide.

16. The method according to claim 15, wherein said reacting 2-(4'-chlorophenyl)ethanol with phosphorous tribromide is carried out in the absence of solvent.

17. The method according to claim 16, wherein said reacting 2-(4'-chlorophenyl)ethanol with phosphorous tribromide comprises:
adding phosphorous tribromide to said 2-(4'-chlorophenyl)ethanol at a temperature of less than about 10° C. to form a bromination reaction mixture; and
heating said bromination reaction mixture to a temperature of about 20° C. to about 30° C. and subsequently to a temperature of about 75° C. to about 85° C.

18. The method according to claim 17, wherein said heating of said bromination reaction mixture to a temperature of about 20° C. to about 30° C. is maintained for about 1 hour to about 3 hours.

19. The method according to claim 18, wherein said heating of said bromination reaction mixture to a temperature of about 75° C. to about 85° C. is maintained for about 2 hours to about 4 hours to form a mixture comprising said 2-(4'-chlorophenyl)ethyl bromide.

20. The method according to claim 19, further comprising the steps:
adding water to said mixture comprising said 2-(4'-chlorophenyl)ethyl bromide at a temperature of about 5° C. to about 20° C. to form a biphasic liquid mixture consisting essentially of an upper aqueous phase and a lower phase comprising said 2-(4'-chlorophenyl)ethyl bromide; and
separating said lower phase comprising said 2-(4'-chlorophenyl)ethyl bromide of said biphasic liquid mixture from said upper aqueous phase of said biphasic liquid mixture.

21. The method according to claim 20, wherein said lower phase comprising said 2-(4'-chlorophenyl)ethyl bromide is substantially pure.

22. A method of resolving a mixture of compounds of Formula (Ia) and (Ib):

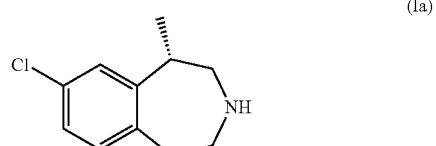

(Ia)

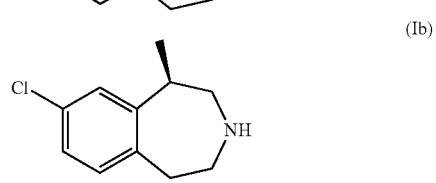

(Ib)

comprising:
contacting said mixture of compounds with L-(+)-tartaric acid in the presence of a solvent comprising acetone to form L-(+)-tartaric acid salts of said compounds;
precipitating said L-(+)-tartaric acid salts of said compounds, wherein the resulting precipitate is enriched with the L-(+)-tartaric acid salt of said compound of Formula (Ia);
dissolving said precipitate in a solution comprising acetone and water at a temperature of about 45° C. to about 60° C. to form a solution containing the dissolved precipitate;
cooling said solution containing the dissolved precipitate to a temperature of about −5° C. to about 10° C.; and
precipitating a second precipitate containing the L-(+)-tartaric acid salt of said compound of Formula (Ia) with an enantiomeric excess of about 98% or greater.

23. A method for preparing (R)-8-chloro-1-methyl-2,3,4,5-tetrahydro-1H-3-benzazepine HCl hemihydrate of Formula (II):

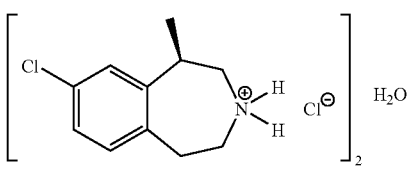

(II)

comprising the steps:
neutralizing (R)-8-chloro-1-methyl-2,3,4,5-tetrahydro-1H-benzo[d]azepinium hemitartrate to form a free base (R)-8-chloro-1-methyl-2,3,4,5-tetrahydro-1H-3-benzazepine;
contacting said free base (R)-8-chloro-1-methyl-2,3,4,5-tetrahydro-1H-3-benzazepine with HCl to form a (R)-8-chloro-1-methyl-2,3,4,5-tetrahydro-1H-3-benzazepine hydrochloride; and
crystallizing said (R)-8-chloro-1-methyl-2,3,4,5-tetrahydro-1H-3-benzazepine hydrochloride in the presence of water to form (R)-8-chloro-1-methyl-2,3,4,5-tetrahydro-1H-3-benzazepine hydrochloride hemihydrate.

24. A method for preparing (R)-8-chloro-1-methyl-2,3,4,5-tetrahydro-1H-3-benzazepine HCl hemihydrate of Formula (II):

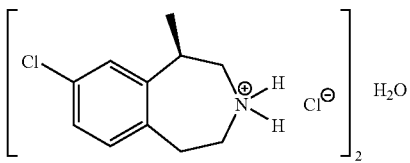

(II)

comprising the steps:
neutralizing 8-chloro-1-methyl-2,3,4,5-tetrahydro-1H-benzoazepinium hemitartrate of the formula:

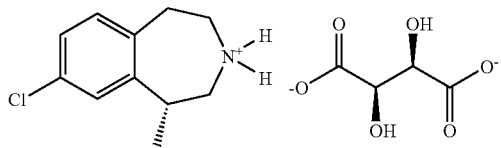

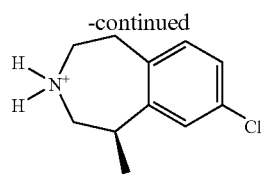

with potassium carbonate in the presence of water and ethyl acetate to form a biphasic liquid mixture consisting essentially of an aqueous phase and an ethyl acetate phase comprising (R)-8-chloro-1-methyl-2,3,4,5-tetrahydro-1H-3-benzazepine of Formula (Ia):

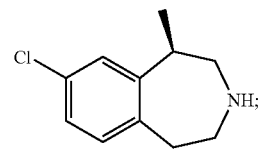

separating said ethyl acetate phase of said biphasic liquid mixture from the aqueous phase of said biphasic liquid mixture;
contacting said ethyl acetate phase with HCl in the presence of water to form an HCl salt of (R)-8-chloro-1-methyl-2,3,4,5-tetrahydro-1H-3-benzazepine, wherein the ratio of water to (R)-8-chloro-1-methyl-2,3,4,5-tetrahydro-1H-3-benzazepine is at least 1 to 2; and
crystallizing said HCl salt of (R)-8-chloro-1-methyl-2,3,4,5-tetrahydro-1H-3-benzazepine to form (R)-8-chloro-1-methyl-2,3,4,5-tetrahydro-1H-3-benzazepine HCl hemihydrate.

25. The method according to claim 24, wherein said biphasic liquid mixture is substantially emulsion-free.

26. The method according to claim 25, wherein said contacting step is carried out at a temperature of about 0° C. to about 25° C.

27. The method according to claim 26, wherein the HCl in said contacting step is in the form of a gas.

* * * * *

UNITED STATES PATENT AND TRADEMARK OFFICE
CERTIFICATE OF CORRECTION

PATENT NO. : 8,168,782 B2
APPLICATION NO. : 12/225966
DATED : May 1, 2012
INVENTOR(S) : Ulrich Weigl et al.

It is certified that error appears in the above-identified patent and that said Letters Patent is hereby corrected as shown below:

In the Specifications

Column 28, lines 30-45, please replace:

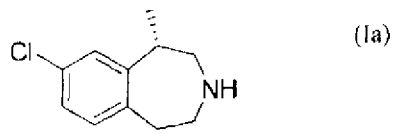 (Ia)

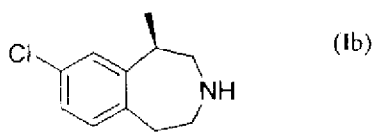 (Ib)

with

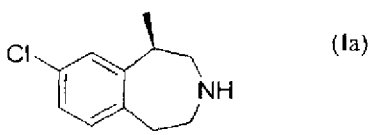 (Ia)

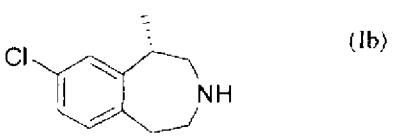 (Ib)

Signed and Sealed this
Seventh Day of May, 2013

Teresa Stanek Rea
*Acting Director of the United States Patent and Trademark Office*